United States Patent
Konukoglu et al.

(10) Patent No.: US 11,503,868 B2
(45) Date of Patent: Nov. 22, 2022

(54) DENIM AND OTHER COMPRESSION GARMENTS AND METHODS FOR FORMING THE SAME

(71) Applicant: Sanko Tekstil Isletmeleri San. Ve Tic. A.S., Inegol-Bursa (TR)

(72) Inventors: Fatih Konukoglu, Inegol-Bursa (TR); Serkan Mert, Inegol-Bursa (TR)

(73) Assignee: Sanko Tekstil Isletmeleri San. Ve Tic. A.S., Inegol—Bursa (TR)

( * ) Notice: Subject to any disclaimer, the term of this patent is extended or adjusted under 35 U.S.C. 154(b) by 392 days.

(21) Appl. No.: 15/898,885

(22) Filed: Feb. 19, 2018

(65) Prior Publication Data
US 2018/0303179 A1    Oct. 25, 2018

(30) Foreign Application Priority Data

Apr. 21, 2017 (EP) ..................................... 17167582

(51) Int. Cl.
| | | |
|---|---|---|
| A41D 31/00 | (2019.01) | |
| A41D 1/06 | (2006.01) | |
| A61F 13/08 | (2006.01) | |
| D03D 15/56 | (2021.01) | |
| A41B 11/00 | (2006.01) | |
| A41B 11/08 | (2006.01) | |
| A41H 43/00 | (2006.01) | |

(Continued)

(52) U.S. Cl.
CPC .............. *A41D 31/00* (2013.01); *A41B 11/00* (2013.01); *A41B 11/08* (2013.01); *A41D 1/06* (2013.01);

(Continued)

(58) Field of Classification Search
CPC ...... A41D 31/00; A41D 1/06; A41D 2300/50; A41D 2400/32; A41D 2500/20;

(Continued)

(56) References Cited

U.S. PATENT DOCUMENTS 3,874,001 A * 4/1975 Patience ................. A61F 13/08
2/240
4,502,301 A * 3/1985 Swallow ................. A61F 13/08
602/62

(Continued)

FOREIGN PATENT DOCUMENTS

EP          3391862 A1 * 10/2018 ............. A61F 13/08

OTHER PUBLICATIONS

International Search Report and Written Opinion dated Mar. 22, 2018 for corresponding application No. PCT/EP2018/054064.

(Continued)

*Primary Examiner* — Gloria M Hale
(74) *Attorney, Agent, or Firm* — Silvia Salvadori

(57) ABSTRACT

Provided is a compression garment formed of a stretchable woven fabric with a uniform elasticity, such as denim. A circumferential portion of the garment surrounds a wearer's body part and is characterized by different degree of stretching but the same circumferential compressive forces when worn by a wearer, at various axial locations due to geometric cuts made to the fabric to form one or more fabric panels, each of which extend along the entire length of the circumferential portion. The compressive forces, degrees of stretching and circumferential lengths of fabric, are calculated using formulas and algorithms that take into account various factors relating to the fabric and the garment being formed.

8 Claims, 13 Drawing Sheets

(51) Int. Cl.
  *D03D 1/00* (2006.01)
  *A41B 1/08* (2006.01)
  *A41B 3/00* (2006.01)
(52) U.S. Cl.
  CPC ............ *A41H 43/00* (2013.01); *A61F 13/08* (2013.01); *D03D 1/00* (2013.01); *D03D 15/56* (2021.01); *A41B 1/08* (2013.01); *A41B 3/00* (2013.01); *A41B 2400/38* (2013.01); *A41D 2300/50* (2013.01); *A41D 2400/32* (2013.01); *A41D 2500/20* (2013.01); *D10B 2401/061* (2013.01); *D10B 2501/021* (2013.01); *D10B 2501/04* (2013.01)
(58) Field of Classification Search
  CPC ........... A41B 11/00; A41B 11/08; A41B 1/08; A41B 3/00; A41B 2400/38; A41H 43/00; A61F 13/08; D03D 1/00; D03D 15/08; D03D 2700/0103; D03D 2700/03; D10B 2401/061; D10B 2501/021; D10B 2501/04
  See application file for complete search history.

(56) References Cited

U.S. PATENT DOCUMENTS

| | | | |
|---|---|---|---|
| 6,430,752 B1 | 8/2002 | Bay | |
| 2005/0113729 A1* | 5/2005 | Scott | A61F 13/085 602/19 |
| 2010/0004563 A1* | 1/2010 | Lipshaw | A61F 13/08 600/587 |
| 2011/0015668 A1* | 1/2011 | Cros | D04B 1/265 606/201 |
| 2011/0257575 A1* | 10/2011 | Farrow | A61F 13/08 602/75 |
| 2012/0100778 A1 | 4/2012 | Cho | |
| 2012/0210487 A1 | 8/2012 | Albin et al. | |
| 2012/0222187 A1 | 9/2012 | McLaren et al. | |
| 2013/0174317 A1 | 7/2013 | Young | |
| 2013/0260129 A1 | 10/2013 | Agzikara et al. | |
| 2014/0165265 A1* | 6/2014 | Tulin | A41D 1/06 2/234 |
| 2016/0076175 A1* | 3/2016 | Rock | A61F 13/08 66/171 |
| 2018/0049482 A1* | 2/2018 | Erkus | A61F 13/08 |

OTHER PUBLICATIONS

Search Report and written opinion dated Mar. 21, 2018 for corresponding application No. EP18157851.9.
Search Report and written opinion dated Nov. 7, 2017 for priority application No. EP7167582.0.
International preliminary report on patentability dated Oct. 22, 2019 for corresponding International application No. PCT/EP2018/054064.
Office Action issued by the European patent Office dated May 21, 2019 for corresponding EP application No. 18157851.9.

* cited by examiner

DENIM AND OTHER COMPRESSION GARMENTS AND METHODS FOR FORMING THE SAME

RELATED APPLICATION

This application is related to and claims priority to European application EP17167582.0 filed 21 Apr. 2017, the contents of which are hereby incorporated by reference as if set forth in their entirety.

TECHNICAL FIELD

The present invention relates most generally to the textile industry and garment production. More particularly, the present invention relates to various stretchable garments with various types of compression characteristics, methods for forming the same and methods for providing compression to a wearer of the stretchable compression garment.

BACKGROUND

Compression garments are textile articles that provide compression to areas of a wearer's body. Compression garments are useful in various medical applications for various purposes such as to improve muscle support and/or to facilitate blood circulation. Compression garments are also popular in sportswear to enhance athletic performance, reduce muscle fatigue and aid in muscle recovery.

Many compression garments designed for medical and therapeutic applications are compression articles such as compression stockings or other garments that circumferentially surround a wearer's body part and are used for treating poor blood circulation, lymphedema, thrombosis or other venous and lymphatic system dysfunctions. US 2011/0257575 and US2005/0113729 teach using a compression garment to treat lymphedema, for example. Compression garments designed for sportswear enhance blood circulation and muscle performance during sport activities. These compression garments help to relieve pain from muscle stiffness and improve blood flow and oxygenation to muscles during and following sport activities. Compression garments for sportswear include shirts, shorts, pants, tights, socks, sleeves for various body parts, and undergarments.

Conventional garments produced by the textile industry include various types of garments with various types of elasticities. Garments with high degrees of elasticity can be obtained using various elastomeric materials such as polyurethanic fibers that can stretch to considerable lengths without breaking. Examples of elastomeric fibers are elastane and spandex and similar materials. Garments with lower degrees of elasticity can be obtained using various different natural or synthetic fibers. The fibers that provide lower degrees of elasticity generally present high recovery properties along with limited elasticity. Various types of fibers with various degrees of elasticity are provided in US patent application Publ. No. 2013/0260129, entitled Composite Stretch Yarn, Process and Fabric.

Compression therapy refers to specially designed garments to manage blood circulation, especially in the feet and legs. Compression socks, in particular, have many great health benefits that not only athletes can benefit from. Wearing compression socks invigorates the legs by oxygenating the blood, boosting the nutrients to that area of the body, reducing pain and weakness, preventing swelling, and helping to regenerate damaged tissues. Compression socks work by gently squeezing gradual compression to the leg, adding pressure to the tissue directly under the skin. By putting pressure on the subcutaneous tissue, excess fluid is encouraged to go back into the capillaries. Compression therapy also prevents superficial veins from causing to overfill with blood by keeping the blood flowing forward.

Candidates for compression therapy could be just about anyone. Some of the main candidates are those who suffer venous diseases. The medical process of getting chronic venous disease relief allows compression socks to prompt valves to work efficiently. Other symptoms or conditions that can be treated by compression theory include surgery, pregnancy, leg injuries, blood clots in veins, prolonged periods with little or no movement, obesity or excessive weight gain, varicose 'spider' veins, and circulation problems due to aging or running or high intensity exercise.

The medical process of chronic venous disease relief allows compression socks to prompt valves to work efficiently. Compression socks help improve a runner's lactate threshold, decreasing the soreness from running. Various studies have shown that compression garments worn during exercise reduce fatigue and muscular pain and they were also proven to reduce deep vein thrombosis (DVT) for airline passengers.

Compression socks and other compression garments for medical applications and for sportswear, are traditionally manufactured by knitting technology but recently, compression socks have become fashionable in colors and styles. Garments formed by knitting include various shortcomings and limitations. One such limitation is that knitting technology is not suitable for many textile processes such as dyeing, washing, laser treatment or various other textile processes. Knitted compression garments are therefore not very useful, rather unfavored and have limited application.

Various knitted compression garments present different levels of compression at different locations of the fabric. In some examples, knitted compression garments for medical applications are used for promoting blood circulation and provide different levels of compression throughout the garment. US2012/0210487 A1 discloses a garment in which one or more regions can include areas in which the elasticity of the garment fabric itself has been reduced. In particular, those regions can include imprinted patterns and the elasticity of fabric portions having the applied pattern is reduced. US2012/0222187 A1 discloses a garment formed of multiple panels and in which the stretchable material of a second panel has higher stretch and recovery characteristics compared to the stretchable material of a first panel. US2012/100778 A1 discloses trousers having parts of the trousers' fabric woven to have different densities so as to generate forces for externally rotating a wearer's leg joints around the pelvis, and US2013/0174317 A1 discloses a compression garment, in particular a full length lower body garment designed for improving circulation, formed of multiple different fabric panels.

US 2014/0165265 provides jeans and a measuring system directed to fitting jeans and actively shaping the jeans to the user's silhouette to provide form-fitting jeans. Different degrees of stretch are achieved by forming multiple different types of garment portions using a polyurethane coating on the inside surface in some regions. U.S. Pat. No. 6,430,752 provides a compression short made of a plurality of strips of elastomeric material sewn together in various diagonal, criss-crossing arrangements.

Multiple fabric panels with different appearances are not aesthetically pleasing due to the multiplicity of the sections that combine to form the garment and the multiplicity of seams between the sections. This is especially problematic in garments desired to be worn by users as a "normal", fashionable garment, i.e. at times other than specifically when working out. Furthermore, there are multiple seams used to join the multiple fabric panels together at various locations and the multiple seams may collectively prove to be uncomfortable to the wearer. The multiple fabric panels with multiple compression intensities are formed from different types of fabrics and produce varying compressive forces. As such, multiple different fabrics are required to form a single compression garment and multiple fabric pieces must be produced and the fabric panels joined together. The requirement of producing a fabric with different properties is also cumbersome and costly. The requirement of multiple different types of fabrics makes it very costly to form a single compression garment.

SUMMARY

The above objects and aims are reached by means of the present invention that provides a compression garment according to claim 1, a method for manufacturing a compression garment according to claim 12, and the use of a compression garment to provide compression to a body part of a wearer as in claim 13.

The invention is based on the principle that different degrees of garment stretching can produce the same circumferential garment compression depending on the circumference of the stretched garment. The degree of stretch of a garment is determined based on the relaxed circumference of a garment and the stretched circumference of the garment, such as when worn by a user. The degree of stretch is associated with a garment compressive force (F) on a stress-strain curve. The garment compressive force (F), together with stretched length or circumference of the user body part (U), determines garment circumferential compression (P), also referred to as garment compression (P), applied by a garment upon a wearer. Because of this relationship, a circumferential portion of a compression garment made of a single fabric material such as a one-ply, uncoated fabric material, can have different degrees of stretching at different axial locations, i.e. different degrees of deformation, yet provide the same garment compression and the invention provides for producing such a garment.

In particular, an object of the invention is to determine necessary garment dimensions based on mathematical relationships, and cut a panel of a woven stretchable fabric with uniform elastic properties accordingly, such that the relaxed circumferential lengths and the degree of stretching of a circumferential portion of the garment vary, but in which the garment circumferential compression (P) applied upon a wearer, is the same at all axial locations of the circumferential portion of the garment. In some embodiments, the relaxed circumferential lengths both increase and decrease multiple times, along the axial direction. In some embodiments, the degree of stretching both increases and decreases multiple times, along the axial direction.

According to some objects, provided is a compression garment (68, 80) comprising a circumferential portion (66) formed of a woven stretchable fabric (10) with uniform elastic properties, and characterized as exhibiting different degrees of stretching at different axial locations of the circumferential portion but providing the same degree of garment compression (P) throughout the circumferential portion, when the compression garment is in a stressed state as worn by a wearer (70).

In some compression garment (68, 80) embodiments, the degree of stretching comprises ((U,stretched−U,relaxed)/U relaxed), where U,stretched comprises stretched circumferential length of the compression garment in a stressed state when worn, and U,relaxed comprises circumferential length of the compression garment in a relaxed state.

Along an axial direction of the circumferential portion (66), values for circumferential lengths (12C, 14C, 16C, 18C, 20C, 22C, 24C, 26C) of the circumferential portion first increase, then decrease, then increase, at least a plurality of times when the compression garment is in a relaxed state in some embodiments.

In some embodiments, the circumferential portion may include undulations (504, 506) in the axial direction when in a relaxed state.

In some embodiments, the circumferential portion may include circumferentially extending ridges (504) along the axial locations when in a relaxed state.

The compression garment may be a single ply, uncoated material.

The circumferential portion (66) may comprise no more than a single panel (2,4) of the woven stretchable fabric.

In some embodiments, the circumferential portion (66) may comprise two panels (2,4) of the woven stretchable fabric (10), joined to form seams that extend along the axial direction (28) of the circumferential portion (66), each the panel extending completely from one longitudinal end to an opposed longitudinal end of the circumferential portion.

The woven stretchable fabric (10) may comprise denim.

In some embodiments, the compression garment may comprise a pair of jeans (68) and the circumferential portion may comprise a thigh portion of a pant leg (60).

The compression garment may comprise compression socks (80) or sleeves that cover the wearer's lower legs.

Another object of the invention is the use of any compression garment (68) described above for treatment of poor blood circulation, lymphedema, thrombosis and other venous and lymphatic system dysfunctions of the wearer.

Another object of the invention provides a method for manufacturing a compression garment. The method comprises: providing an uncoated stretchable woven fabric (10); cutting (1005) the single-ply, uncoated stretchable woven fabric (10) to form at least one panel (2, 4) thereof, and forming (1007) a circumferential portion (60) of the compression garment (68) in which each the at least one panel (2, 4) extends to opposed longitudinal ends of the circumferential portion, wherein the circumferential portion exhibits different degrees of stretching but applies the same degree of circumferential garment compression (P) at different axial locations (12, 14, 16, 18, 20, 22, 24, 26), when the compression garment is in a stressed condition when worn by a wearer (70).

In some embodiments, the method includes wherein the cutting comprises cutting the single-ply uncoated stretchable woven fabric (10) to produce circumferential lengths that increase, then decrease, then increase (225, 227, 229), at least a plurality of times, along an axial direction, when the circumferential portion is in a relaxed state.

In some embodiments, the method includes the cutting forming a single panel having a seam (65) that extends in the axial direction (62).

In some embodiments, the method includes the cutting forming two the panels (2, 4) joined to form seams that extend in an axial direction of the circumferential portion (60).

In some embodiments, the method includes the uncoated stretchable woven fabric being a single-ply uncoated stretchable woven fabric, with uniform elasticity.

In some embodiments, the method includes the stretchable woven fabric (10) being denim.

In some embodiments, the method includes the compression garment comprising a pair of jeans (68).

In some embodiments, the method includes the compression garment comprising compression socks (80).

In some embodiments, the method includes the different degrees of stretching including degrees of stretching that increase then decrease then increase along at least one group of three successive axial locations (14, 16, 18) of the axial locations, when the compression garment is in the stretched state as worn by the wearer (70).

In some embodiments, the method comprises calculating (1003) a plurality of relaxed circumferential fabric lengths to produce the same degree of garment circumferential compression (P) exerted on a wearer's body part when the circumferential garment portion is in the stretched condition when worn by a typical wearer, at each of the plurality of the different axial locations (12, 14, 16, 18, 20, 22, 24, 26) according to equation (1), $$Pi = \frac{20\pi^* F_i}{U_i} \quad (1)$$

wherein P=garment circumferential compression in kPa, F=garment compressive force in N/cm and U=body part circumference in cm, at each measuring point i associated with a corresponding one of the plurality of the different axial locations of the compressive garment portion,
and wherein the cutting is based on the calculating and produces the plurality of relaxed circumferential fabric lengths.

In some embodiments, the method further comprises forming (2005) a model circumferential garment portion using at least one panel of the single-ply, uncoated stretchable woven fabric (10); measuring (2007) a relaxed circumferential length of the model circumferential garment portion in a relaxed condition, at each of the plurality of the different axial locations; stretching (2011) the model circumferential garment portion by placing the model circumferential garment portion on a body model member having known circumferential lengths at each the axial location, to provide a plurality of stretched circumferential lengths (U) (2013); and calculating (2023) the garment compressive force (F) based on the degree of stretching using a stress-strain relationship of the single-ply, uncoated stretchable woven fabric at each the axial location.

In some embodiments, the method comprises the known circumferential lengths of the body model member or dimensions being associated with a size chart for a particular wearer size, and further comprises forming (2005) a model circumferential garment portion using at least one panel of the single ply, uncoated stretchable woven fabric (10); measuring (2007) a relaxed circumferential length of the model circumferential garment portion in a relaxed condition, at each of the plurality of the different axial locations; stretching (2011) the model circumferential garment portion by placing the model circumferential garment portion on a body part model having known circumferential lengths at each the axial location, to provide a plurality of stretched circumferential lengths (2013); measuring (2019) the garment compression P at each axial location of said model circumferential garment portion; and calculating (2023) a garment compressive force F based on the measured garment compression P, at each said axial location; calculating (2015, 2017) a degree of stretching at each said axial location using the stretched circumferential lengths and the relaxed circumferential lengths; determining (2029) fabric compressive force f at each said axial location using a stress-strain curve of the stretchable single layer woven fabric (10) and the calculated degrees of stretching at each axial location; determining (2031) a seam correction factor by comparing the calculated garment compressive force F to the determined fabric compressive force f; determining (2039) a required garment compressive force F,required, to produce the desired garment compression at each said axial location; converting (2043) the required garment compressive force F,required to a required fabric compressive force f at each said axial location by multiplying the required garment compressive force F by the seam correction factor; and determining (2051) the circumferential fabric lengths using the required fabric compressive force f and the stress-strain curve.

BRIEF DESCRIPTION OF THE DRAWING

Further aspects and advantages in accordance with the present disclosure will be discussed more in detail with reference to the enclosed drawings, given by way of non-limiting example, wherein.

DETAILED DESCRIPTION

Figure 1:
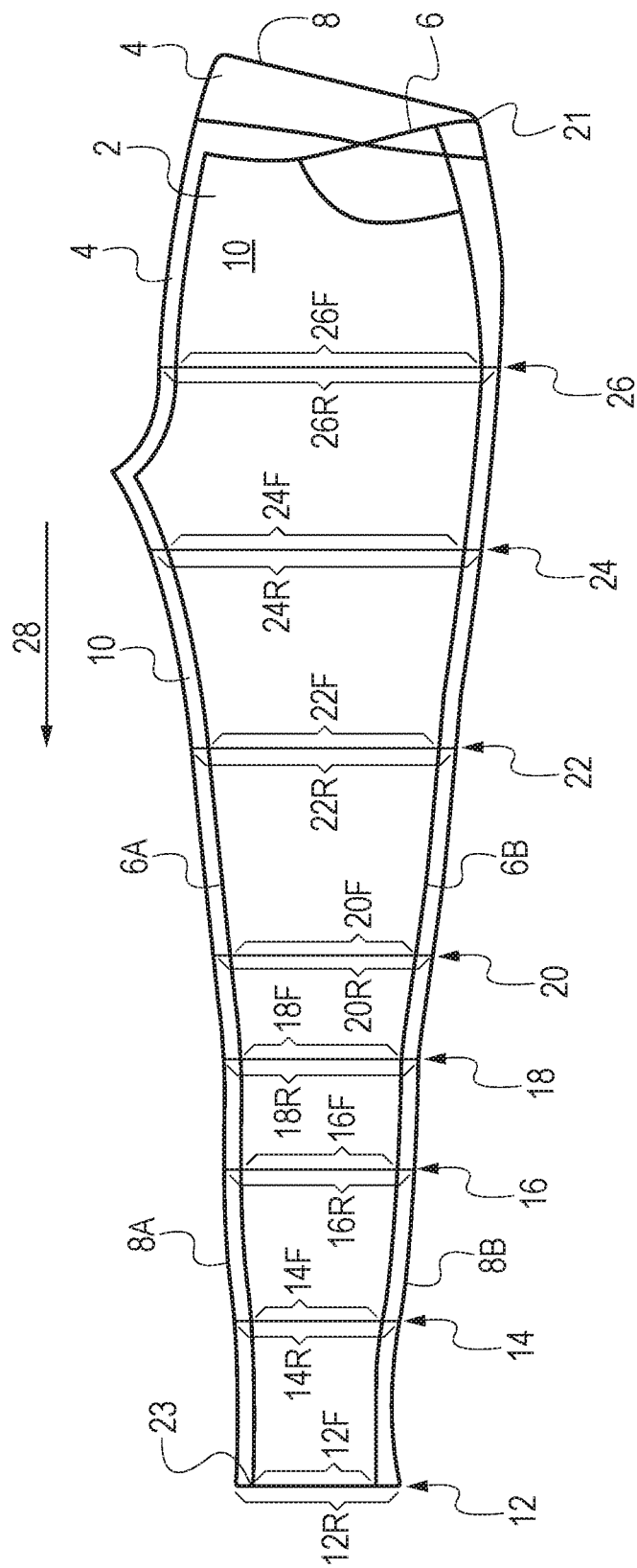
FIG. 1 shows two pieces of stretchable fabric such as may be combined to form a pant leg for a pair of jeans. Each of the two pieces of stretchable fabric has geometric cuts made according to aspects of the invention.

In some embodiments, the disclosure provides a compression garment formed of a stretchable fabric. The garment includes at least one circumferential portion that surrounds a wearer's body part such as an arm, leg, foot, abdomen or a part thereof. In some embodiments, the garment or at least the circumferential portion of the garment is formed of a single fabric. In some embodiments, the stretchable fabric itself has a uniform, i.e. constant, elasticity while in other embodiments, the elasticity changes throughout the fabric. The garment may advantageously be a denim garment and according to various advantageous embodiments of the disclosure, the compression garment is a pair of socks or a pair of pants, or trousers. The garment provides degrees of compressive force that may be uniform throughout the garment, or that may vary at different axial locations of the circumferential portion, when the garment is worn by a typical wearer, i.e. when the garment is stressed.

The stretchable fabric with the uniform elasticity, may be a single-ply, uncoated fabric and the circumferential portion may be formed of a single panel or it may be formed of a plurality of panels, each panel extending along the entire axial direction of the circumferential portion The circumferential garment with the compressive forces that may be uniform throughout the compression garment or that may vary along different axial locations of the compression garment, does not require multiple pieces of fabric joined to one another along the axial or longitudinal direction. Rather, a single piece of fabric or two pieces of fabric coupled laterally to form seams that extend in the longitudinal, i.e. axial direction, may be used to produce garment compression that may be uniform or which may vary at different axial locations. The fabric panel or each of the fabric panels may extend completely from one longitudinal end to the opposed longitudinal end of the circumferential portion. In some embodiments, multiple fabric panels may be made from a woven stretchable fabric type, i.e. each of the fabric panels is formed of the same material such as a fabric having uniform elasticity, and may be combined to form a circumferential portion of a compression garment.

According to an aspect of the invention, a method for treatment of poor blood circulation, lymphedema, thrombosis or other venous and lymphatic system dysfunctions of a human or other animal, is provided. The method includes manufacturing the compression garment according to various aspects of the invention and the wearer wearing the circumferential portion of the compression garment.

An aspect of the invention provides for the use of a garment as above, as used in the treatment of poor blood circulation, lymphedema, thrombosis or other venous and lymphatic system dysfunctions of a human or other animal According to an aspect of the invention, a method for calculating dimensions and making corresponding geometric cuts to produce a circumferential portion of a garment with desired garment compression at various axial locations, is provided.

The compression garment includes a circumferential portion that may be "characterized" as having a plurality of circumferential bands at different axial locations of the circumferential portion although each of the "bands" is formed of the same fabric material or materials. In other words, regardless of the axial location of the so-called "bands" each of the respective bands is formed of a single fabric material according to embodiments in which the circumferential portion is formed of one fabric panel or each of the so-called "bands" is formed of two circumferentially joined panels that combine to form the circumferential portion. In some embodiments, the fabric panel of the circumferential portion extends completely from one longitudinal end to the opposed longitudinal end of the circumferential portion. The circumferential bands may advantageously be tailored to provide uniform compression throughout the circumferential portion, i.e. each of the circumferential bands provides the same compression. The circumferential bands may exhibit different degrees of stretching, or the same degree of stretching when the compression garment is worn by a typical wearer.

In preferred embodiments, there are different degrees of stretching at the various axial locations but the degree of garment circumferential compression (P) applied to a wearer, is the same. "Degree of stretching" refers to the stretched length of a fabric at a particular time compared to the length of the fabric in a relaxed state.

The term wearer and the expression "typical wearer" as used herein, are used to refer to a human having body part dimensions that are substantially equal to body part dimensions for an associated industry standard size chart associated with a particular size of a particular garment. In some embodiments, the typical wearer is a wearer having an anatomy defined by shapes, sizes and relative sizes falling within a range of normal shapes, sizes and relative sizes typically associated with a particular garment size and type, i.e. within an average or normal range for a person that wears a particular garment type and size.

The compressive force exerted by the compression garment is a circumferentially applied force experienced when the garment is worn by the wearer, i.e. when the circumferential portion of the compression garment is in its stressed state and if referred to as garment compression (P).

Uniform compression provides the same amount of compression to all parts of the wearer's body part, e.g. the leg. Uniform compression has been found to offer more overall support, relief and preventive measures for future leg issues.

The disclosure provides for making geometric or other cuts to the fabric to produce at least one panel of the fabric. The panel may have at least one non-linear edge. The panel is joined to another panel or to another edge of the same fabric panel to form a circumferential portion of a compression garment. When in a relaxed state such as when not being worn, the circumferential portion may exhibit undulations along the axial direction, i.e. when viewed along the axial direction there may be a succession of ridges. In one embodiment, the elasticity of the fabric is uniform throughout the fabric itself and the garment so formed, includes uniform garment compression at all locations, including anatomical locations with different circumferences, when worn by a wearer. In this embodiment of a uniform elasticity garment, the degree of stretching will vary at the different axial locations to produce the same degree of garment compression throughout the circumferential portion due to geometric cuts that are made to produce specified fabric dimensions and compression levels, at various locations along the garment. In other words, the uniform compression at various locations, is obtained by designing the garment to have dimensions that will result in different degrees of stretching when the garment is worn by the user in accordance with this embodiment. Garment compression is compressive force and is a circumferential compression, i.e. a compressive force exerted in the circumferential direction.

By "the same garment compression" or the "same degree of garment compression" or "the same compression", it is meant throughout the disclosure, that the compression value is substantially the same, e.g. it varies no more than +/−5%, for example.

In other embodiments, the garment compression varies at different locations of the circumferential portion due to different or the same degrees of stretching, when worn by a wearer.

In one aspect, the disclosure provides a stretchable fabric with uniform, i.e., constant or non-uniform elasticity, and a method for making geometric or other cuts to the fabric to produce at least one panel of the fabric. The geometric cuts are determined by a calculation that takes into account various factors relating to the fabric and the garment being produced. The produced fabric may have edges with any of various shapes such as at least one non-linear edge and will have particular dimensions at various locations that are determined by an engineered pattern design.

The panel is joined to another panel or to another edge of the fabric, to form a seam and a compression garment or a circumferential portion of a compression garment, that may include a uniform compressive force at all axial locations including embodiments in which the elasticity of the fabric is uniform throughout the fabric or in which it varies. The described circumferential portion of the compression garment does not require multiple fabric panels disposed along and joined to one another along the longitudinal direction of the circumferential portion.

The compression garment includes a circumferential portion that surrounds a wearer's body and includes desired compressive forces ("garment compression") calculated for various locations along the axial direction and therefore at various locations of the human anatomy that have different circumferential lengths, when worn by a wearer.

The cuts are based on an engineered pattern design that provides particular garment dimensions at various locations calculated to produce desired degrees of stretching and provide desired compression effects at various locations of the garment, when the garment is worn. The geometric cuts may produce a fabric panel with one or more custom tailored edges. When the fabric panel is used to produce a compression garment such as by joining two edges of the fabric panel together to form a circumferential portion, the circumferential portion includes desired degrees of garment compression at various locations, when worn. The circumferential portion may exhibit undulations along the axial direction in a relaxed state, i.e. when viewed along the axial direction there may be a succession of ridges and, when worn, the circumferential portion stretches to different degrees, yet provides the same garment compression.

The garment compression (P) exerted at any circumferential location depends upon the type of fabric, the degree of stretching of the garment and also the circumference of the anatomy of the wearer, at that location.

The calculation used to determine the geometric cuts, is based upon a number of factors and may utilize a formula or algorithm to create a desired pattern for the geometric cuts. The factors may include the stress-strain characteristics of the fabric, the desired compression class, size or measurement charts for the garment which may be based on brand, correction factors such as seam corrections and various other corrections and compression standards. Various diagrams may be generated using various algorithms and mathematical formulas that take into account the above and other factors.

In some aspects, the manufacturing method includes calculating the plurality of circumferential fabric lengths to produce a desired garment compression, P, exerted on a typical wearer's body part when the circumferential garment portion is in a stretched condition when worn by a typical wearer, at each of a plurality of the different axial locations according to equation (1), $$Pi = \frac{20\pi^* F_i}{U_i} \quad (1)$$

wherein P=garment compression in kPa, F=garment compressive force in N/cm and U=body part circumference in cm, at each measuring point i associated with a corresponding one of the plurality of the different axial locations of the compressive garment portion. Garment cuts are made based on these calculations, as will be described below.

Various kinds of compression garments are formed in accordance with the embodiments of the disclosure and the circumferential portion of the garments may be a sleeve or a portion of a sleeve including knee sleeves and leg sleeves, a pant leg, a sock, a shirt, collar or various other portions. In some embodiments, the compression garment itself is a circumferential garment, i.e. a garment that surrounds a body part of the wearer such as socks or sleeves including knee sleeves and leg sleeves. In some embodiments, the disclosure provides compression socks that extend up to a wearer's knee but compression socks of other lengths are also provided. In some embodiments, the "compression socks" are actually sleeves that extend from the wearer's ankle to knees, i.e. they do not encompass the wearer's foot. In some embodiments, the disclosure provides a compression device such as a wrist support, elbow support, knee support, or ankle support. In some embodiments, the compression garment is a pair of tights. In some embodiments, the compression garment is a fashion garment for every day wear. In some advantageous embodiments, the compression garment is a pair of pants formed of stretchable denim and in various embodiments, the denim pants include an increased compression level at the ankle and a decreasing compression in the upward direction along each pant leg. In other advantageous embodiments, the compression garment is a pair of pants or compression socks formed of stretchable denim and in which the degree of stretching and the garment compression (P) is constant throughout the circumferential garment.

FIG. 1 shows two panels of fabric such as may be combined to form a pant leg for a pair of pants or jeans. Although FIG. 1 shows two panels of fabric that combine to form a pant leg, it should be understood that in various other embodiments, the fabric panels formed using the garment length calculations and the geometric cuts according to the disclosure, may be used to form other circumferential garments and circumferential garments portions, such as described above. The panel or panels may take on various other shapes and be used to form various other garments and apparel in other embodiments.

FIG. 1 shows front panel 2 and rear panel 4 such as may be combined to form a pant leg for a pair of trousers, i.e. jeans or pants. Front panel 2 is defined by cut edges 6 and rear panel 4 is defined by cut edges 8. In the illustrated embodiment, each of front panel 2 and rear panel 4 is formed of fabric 10. Fabric 10 may be any suitable stretchable fabric such as described herein. Fabric 10 may be a single-ply uncoated material with uniform elasticity throughout. In advantageous embodiments, fabric 10 may be characterized by having constant elasticity through the fabric. In some uniform elasticity embodiments, the elasticity in the warp direction may vary from the elasticity in the weft direction and in other embodiments, the elasticity is the same in both the warp and weft directions. In other embodiments, the elasticity varies throughout fabric 10. In some embodiments, fabric 10 is an untreated fabric. In some embodiments, fabric 10 is an uncoated fabric and in some embodiments, fabric 10 is an untreated and uncoated fabric. In other embodiments, more than two pieces of fabric panels may be formed from fabric 10, i.e. formed from the same fabric type with uniform elasticity, and may be combined to form a circumferential portion of a compression garment, each panel extending along the entire length of the formed circumferential portion. According to some of the aforementioned or subsequently disclosed embodiments, either or both of front panel 2 and rear panel 4 may include a uniform elasticity or either or both may include a nonuniform elasticity.

In some embodiments, fabric 10 is advantageously a woven stretchable fabric. Fabric 10 may be a blended woven fabric material with inelastic and elastic fibers. Fabric 10 is stretchable woven denim according to various advantageous embodiments but in other embodiments, fabric 10 may be one of any of various other suitable stretchable fabrics.

Fabric 10 may be formed of various types of elastomeric fibers that provide high degrees of elasticity such as elastane and spandex and other similar materials. Fabric 10 is advantageously a single-ply or single layer of material. Some examples of elastomeric fibers that may be used in fabric 10 and provide low degrees of elasticity include natural and synthetic fibres such as polyester, rayon, nylon, polyesters and elastomultiesters such as PBT and the bicomponent polyesters Poly(Trimethylene Terephthalate)/Polyethylene Terephthalate (PTT/PET). The identified elastomeric fibers are provided by way of example only and in various embodiments, any of various other suitable elastomeric fibers or combinations of different elastomeric fibers may be used to form fabric 10. The elastic fibers may be formed of the same or different material and with the same or different degrees of elasticity. In some embodiments in which two elastic fibers are used to form yarns of fabric 10, one of the elastic fibers may be stretchable to a length of 400% of its original length and one of the elastic fibers is less elastic but stretchable to about 20% of its original length. In other embodiments, the fibers used to form fabric 10 represent other combinations of fibers that have different degrees of elasticity. In some embodiments, fabric 10 is formed of thermoplastic elastic fibers. In some embodiments, thermoplastic elastomers and thermoplastic polyurethanes (TPU) having a well-combined structure of soft and hard building segments that provides exceptional elasticity, are used. Various elastic polyurethane materials, collectively referred to as elastanes, may be used.

Fabric 10 is a single ply layer of fabric material and may be formed of various fibers that combine to form various yarns that include multiple fibers. In some embodiments, both inelastic and elastic fibers extend in both the warp and weft directions of fabric 10. In some embodiments, elastomeric material may be cast into mono-filaments and/or into staple fibers and may be utilized as-is or together with other fibers in a yarn. In some embodiments, fabric 10 is formed of elastic yarns that include an elastic core of one or more elastic fibers and having an inelastic sheath covering the core. In one particular embodiment, the elastic core includes two elastic fibers, one being stretchable to a length of 400% of its original length and the other being less elastic but stretchable to about 20% of its original length. In other embodiments, the fibers used to form fabric 10 represent other combinations of fibers that have different degrees of elasticity. The inelastic sheath may be formed of cotton or other natural or synthetic materials. Various methods for forming a yarn by combining a stretchable core including one or multiple fibers that have elastic properties, with an insulating sheath covering, are provided in US patent application Publ. No. 2013/0260129, the contents of which are hereby incorporated by reference as if set forth in their entirety. In some elastic core yarn embodiments, the core includes a bundle of one or multiple fibers, some or all of which are elastic. The fibers that make up the core may be joined together by twisting, intermingling or co-extrusion. In embodiments in which the fibers are intertwined, they may be intertwined to various degrees. The elastomeric core is characterized by excellent recovery and resiliency properties provided by one or more of the core fibers.

Core-spun and ring spun technologies are known and widely used processes in the textile industry, and involve combining two or more fibers with different features, to form one yarn member. These and various other methods for spinning fibers to produce yarns may be used to form fabric 10.

Fabric 10 may also be formed of the following types of fabrics that may be used to produce compression garments according to various embodiments of the disclosure. Undyed fabrics, and all types of dyed fabrics such as indigo, reactive, pigment, and sulphur overdyed fabrics may be used as fabric 10. Fabrics that have fibers such as cotton together with any selulosic fiber blends such as viscose, rayon, modal, cupro (branded fibers like tencel), may be used as fabric 10. Natural fiber blends such as linen, wool, cashmere and the like, may be used as fabric 10. Blends of cotton and man-made fibers such as polyesther, pbt, naylon 6.0, nylon 6.6 (for example, branded fibers like cordura, t400 and the like) may be used to produce fabric 10 according to embodiments of the disclosure. Various fabrics made using man-made fibers as staple or filament fibers such as polyesther, nylon, etc. may be used. Various types of woven fabrics such as plain weaves, twills, canvas (panama), sateen and dobby type woven fabrics made with the above mentioned fibers may be used as fabric 10. Stretch woven fabrics such as with elasthane in the weft direction, the warp direction and in both the weft and warp directions or stretch knitted fabrics with elastomeric fibers such as elasthane, pbt, t400, polyesther, and the like, may be used. In some embodiments, fabric 3 is a fabric with a fabric weight ranging from 1 oz/sqyd (33.906 gr/sqm) to 14 oz/sqyd (474 gr/sqm) but various other fabric weights are used in other embodiments.

In some embodiments, both front panel 2 and rear panel 4 are formed of the described fabric 10 and in such embodiments in which both of front panel 2 and rear panel 4 are formed of the same fabric, the fabric, i.e. fabric 10 may advantageously have uniform elasticity. In other embodiments, only front panel 2 or only rear panel 4 is formed of the described fabric 10. According to one embodiment, one panel formed of fabric 10 having uniform elasticity, is joined to a fabric of a different material to form a pant leg or other circumferential compression garment or garment portion, such that the circumferential compression garment or garment portion is formed of the same fabric panel or fabric panels at each axial location, i.e each panel extends completely from one longitudinal end to the other of the circumferential garment or garment portion.

Still referring to FIG. 1, front panel 2 is defined by cut edges 6 and throughout the longitudinal and, eventual, axial direction of front panel 2 (axial direction 28), front panel 2 is defined by opposed edges 6A and 6B. Similarly, rear panel 4 is defined by cut edges 8 and throughout the longitudinal and, eventual, axial direction of rear panel 4, rear panel 4 is defined by opposed edges 8A and 8B. The dimensions of the respective panels, i.e. front panel 2 and rear panel 4, i.e. the distance between opposed edges 6A and 6B, and the distance between opposed edges 8A and 8B respectively, are determined based on the engineered pattern design of the invention and are designed to provide desired compression effects and a desired dimension in the circumferential direction, when panels 2 and 4 are combined to form a pant leg. Once the dimensions are determined at the various locations, the geometric cuts are made to produce the determined dimensions of the garment, such as will be shown in FIG. 5.

In other embodiments, a single panel is used to form a pant leg with only one seam and the geometric cuts made to produce the determined dimensions, may be used to form the single panel. According to this embodiment, the single panel of material has its opposed longitudinal edges joined to one another to form a seam thereby creating a circumferential compression garment, such as a pant leg.

According to various embodiments, fabric 10 is a single layer i.e. single ply of a fabric. The circumferential portion is a compressive circumferential portion, i.e. it exerts a circumferential compression when stressed as worn by a wearer. This circumferential compression exerted by the worn garment is called garment compression (P) and may be measured in kPa. The compressive circumferential portion applies compression and is void of any significant overlap portions of the panels although, of course, the seam may include a slight overlap portion between two fabric panels. In various embodiments of the invention, various seam types may be used such as but not limited to seams formed by and referred to as a lock stitch, chain stitch, safety stich, surging stitch, overlapped stitch, zigzag stitch, cover stitch, blind stitch, merrow stitch, flat lock stitch, heat seam seal with an adhesive tape, ultrasonic welding, laser welding, or various combinations of the preceding. The compressive circumferential portion formed of a single layer of woven stretchable fabric is characterized as being void of any elastomeric straps or other compressive features or straps or coatings attached to or laminated upon the compressive circumferential portion. The compressive circumferential portion also does not include any fabric or other extensions that extend in a direction acute or orthogonal to the plane of the fabric and that produce a fabric having uneven thickness.

According to various of the aforementioned embodiments, the two panels such as rear panel 4 and front panel 2 or a single panel, each extend completely along the longitudinal length, i.e. the length of the garment along the longitudinal direction 28, i.e. from one longitudinal end 21 to the opposed longitudinal end 23 of a circumferential portion formed only from the panels 2 and 4.

According to some embodiments, more than two panels of the same fabric having a uniform elasticity may be arranged to each extend completely along the longitudinal direction to create the circumferential compression garment. In other words, fabric 10 which may have uniform elasticity, is cut into multiple fabric panels that combine to form a circumferential portion of a compression garment in which each of the multiple fabric panels extend from one end to the other end of the circumferential portion and in which the compression applied in the circumferential direction is produced only by the circumferential portion formed of the fabric panels, i.e. without any inner or outer compressive straps or other features.

In FIG. 1, either or both of front panel 2 and rear panel 4 may be cut at various angles with respect to the warp and weft directions of the fibers of fabric 10 in various embodiments.

Opposed edges 6A and 6B of front panel 2 are non-linear edges formed by making a geometric cut of fabric 10 as in the illustrated embodiment. Also in the illustrated embodiment, opposed edges 8A and 8B of rear panel 4 are non-linear edges formed by making a geometric cut of fabric 10. By "non-linear" it is meant that the respective edge is not a continuously linear edge, i.e. not a continuously straight edge, although one or more of the respective edges may include multiple linear segments. In some embodiments, either or both of front panel 2 and rear panel 4, are jagged in shape and the edges of front panel 2 and rear panel 4 are not a continuously gradually smooth edge. In other embodiments, one of the opposed edges is straight edge and the other edge will have more exaggerated cuts. In some embodiments, one or more of edges 6A, 6B, 8A and 8B is linear as the dimensions are determined at various locations using the methods described herein.

In various embodiments, edges 6A, 6B, 8A, 8B include a number of sections of straight portions and a number of section of curved portions. In some embodiments, the straight portions include adjacent straight portions that are angled with respect to one another and therefore do not combine to form a continuously straight edge. In some embodiments, one or more or the edges 6A, 6B, 8A, 8B are nonlinear edges formed of only a number of straight edge portions and in some embodiments, one or more or the edges 6A, 6B, 8A, 8B include at least one curved portion connecting straight portions. In some embodiments, the entire edge 6A, 6B, 8A, or 8B is a continuously curved edge, and the edge curves may curve in and out periodically or regularly. In some embodiments, the entire edge 6A, 6B, 8A, 8B is a continuously straight edge. In some embodiments, the opposed edges, for example opposed edges 8A, 8B of rear panel 4, are parallel to each other. This may be true for either or both of front panel 2 and rear panel 4. In other embodiments, the opposed edges, for example opposed edges 6A, 6B of front panel 2, are each straight but angled with respect to one another. This applies to either or both of front panel 2 and rear panel 4. In some embodiments, one or more of edges 6A, 6B, 8A, 8B includes both curved portions and straight portions and the straight portions may extend along a significant length of the panel, i.e. from location 12 to location 24 in some embodiments. Edges 6A, 6B, 8A, 8B may each take on any of various nonlinear shapes such as zigzag or curved and the configuration of the nonlinear edge may include regularly repeating sections or an irregular edge.

In FIG. 1, each of front panel 2 and rear panel 4 is shown to have a number of locations 12, 14, 16, 18, 20, 22, 24, and 26, somewhat arbitrarily designated to aid in explaining aspects of the present disclosure and, as such, the eight locations are primarily for illustrative purposes. In some embodiments, the measurement locations may represent industry-standard locations for calculating garment dimensions. A garment length necessary to produce a desired compression is calculated for each of locations 12, 14, 16, 18, 20, 22, 24, and 26 and the fabric is cut accordingly. According to various embodiments, there is no physical difference in the fabric material in any of the so-identified "locations," other than the dimensions as can be seen and the elasticity or other aspects of the fabric material is constant throughout the respective, i.e. either or both of front panel 2 and rear panel 4.

In FIG. 1, front panel 2 has particular widths at the various locations 12, 14, 16, 18, 20, 22, 24, and 26 associated with non-linear opposed edges 6A and 6B as illustrated. Rear panel 4 has particular widths at the various locations 12, 14, 16, 18, 20, 22, 24, and 26 associated with non-linear opposed edges 8A and 8B as illustrated. The eight arbitrarily designated regions 12, 14, 16, 18, 20, 22, 24, and 26 are regions designated to be associated with a particular shape, configuration or location of the respective opposed edges.

According to embodiments in which a much higher number of designated regions are used, a higher number of particular widths are determined, and therefore a greater number of segments between the designated regions will exist and may produce a more smoothed-out looking edge, such as a curved edge.

Figure 2:
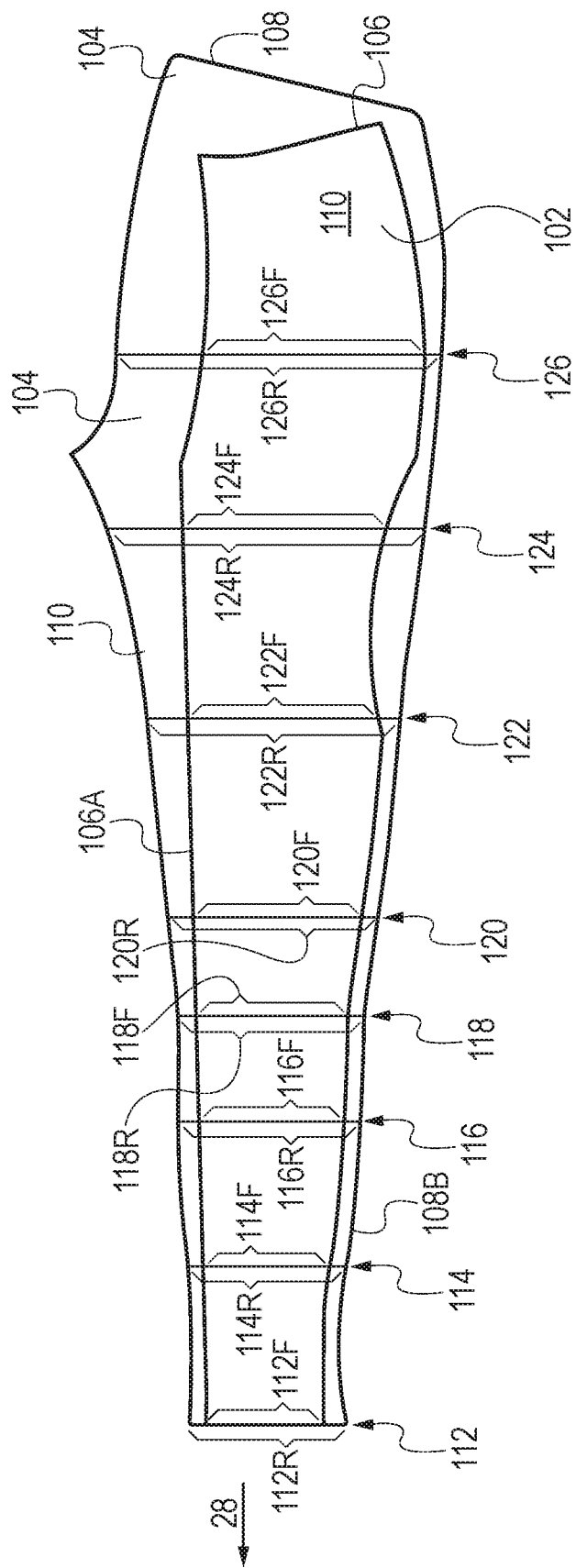
FIG. 2 shows another embodiment of two pieces of stretchable fabric such as may be combined to form a pant leg for a pair of jeans. Each of the two pieces of stretchable fabric is cut according to aspects of the invention.

FIG. 2 illustrates another embodiment of geometric cuts used to produce opposed edges of a front panel and rear panel. In FIG. 2, front panel 102 has particular widths at the various locations 112, 114, 116, 118, 120, 122, 124, and 126 associated with opposed edges 106A and 106B as illustrated. Portions of opposed edges 106A and 106B are straight and angled with respect to one another and portions of opposed edges 106A and 106B are curved. Rear panel 104 has particular illustrated widths at the various locations 112, 114, 116, 118, 120, 122, 124, and 126 in association with the non-linear nature of opposed edges 108A and 108B as illustrated. The eight designated regions 112, 114, 116, 118, 120, 122, 124, and 126 are regions designated to be associated with a particular shape, configuration or location of the respective opposed edges but represent only a portion of the locations at which a dimension was calculated. For example, at locations where edge 108B, for example, is curved, multiple calculations were made at locations close to one another to produce the smooth effect.

In FIG. 2, at each of locations 112, 114, 116, 118, 120, 122, 124, and 126 and many others, the geometric cuts determined according to the disclosure are made to produce the desired dimensions, i.e. dimensions 112R, 114R, 116R, 118R, 120R, 122R, 124R, 126R and dimensions 112F, 114F, 116F, 118F, 120F, 122F, 124F, and 126F at the corresponding locations 112, 114, 116, 118, 120, 122, 124 and 126. In some embodiments, most or all of dimensions 112R, 114R, 116R, 118R, 120R, 122R, 124R, 126R differ from one another and in some embodiments, most or all of dimensions 112F, 114F, 116F, 118F, 120F, 122F, 124F, and 126F differ from one another.

Figure 3:
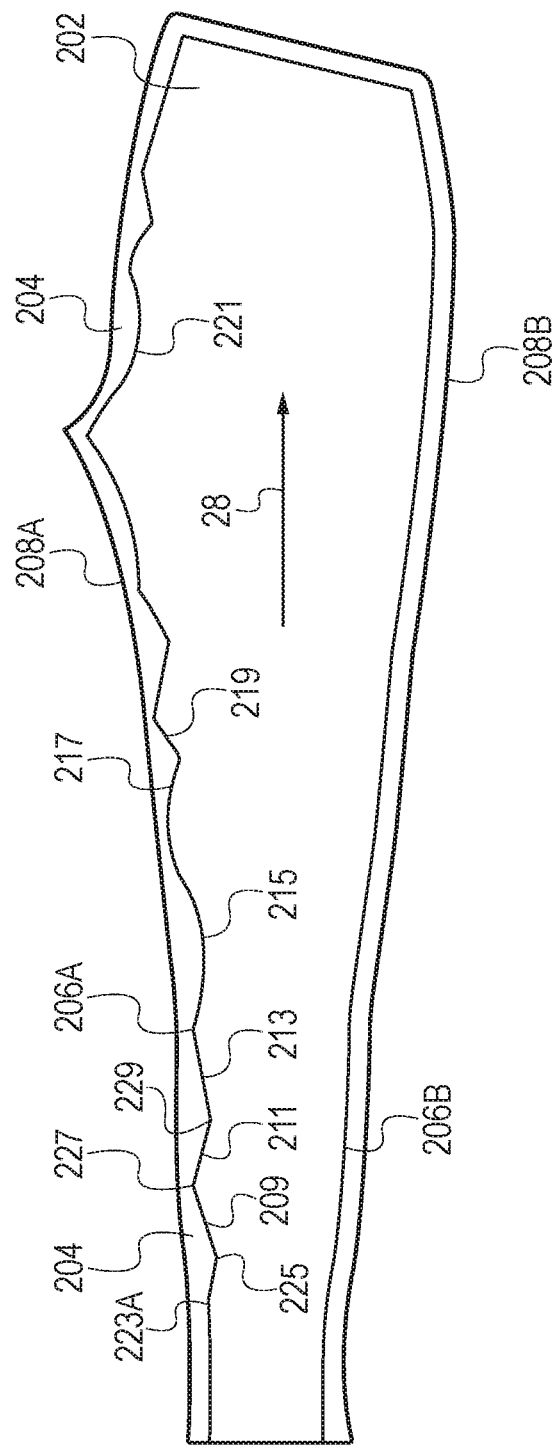
FIG. 3 shows yet another embodiment of two pieces of stretchable fabric such as may be combined to form a pant leg for a pair of jeans. Each of the two pieces of stretchable fabric is shaped according to aspects of the invention.

FIG. 3 shows other aspects of the geometric cuts made in accordance with the invention. In FIG. 3, front panel 202 is defined by opposed edges 206A and 206B and rear panel 204 is defined by opposed edges 208A and 208B although the particular locations at which the garment lengths were determined, are not shown. Edge 206A includes multiple straight segments and curved sections. The curved sections may result from using a high number of axial locations spaced close together at which garment length is determined. Edge 206A, for example includes adjacent linear segments 209, 211 and 213 that are each angled with respect to each other and also shows straight segment 219 adjacent to and angled with respect to curved portion 217. Curved portion 215 is adjacent and angled with respect to linear segment 213. By "angled with respect to each other," it is meant that they are not co-linear. Edges 206A and 206B will be joined to edges 208A and 208B, respectively, to form the circumferential garment. Proceeding along axial direction 28, it can be seen that the width of front panel 202 both increases and decreases along three successive axial locations 225, 227 and 229. The width of front panel 202 decreases from point 223 to point 225, then increases between location 225 and location 227 then decreases between location 227 and location 229, and so on. When a compression garment is formed by joining front panel 202 and rear panel 204, the circumferential garment portion will be characterized by the circumferential length increasing and decreasing accordingly. In a relaxed state such as when not worn, such a circumferential portion may have a ridged, undulating appearance (see FIG. 5A).

According to any of the preceding embodiments, each of the opposed edges 6A, 6B, 8A, 8B, 106A, 106B, 108A, 108B, 206A, 206B, 208A, 208B is custom tailored by calculating desired dimensions at a plurality of various locations. Referring again to FIG. 1, at each of locations 12, 14, 16, 18, 20, 22, 24, and 26, the geometric cuts determined according to the disclosure are made to produce the desired dimensions, i.e. dimensions 12R, 14R, 16R, 18R, 20R, 22R, 24R, 26R and dimensions 12F, 14F, 16F, 18F, 20F, 22F, 24F, and 26F at the corresponding locations 12, 14, 16, 18, 20, 22, 24. In some embodiments, most or all of dimensions 12R, 14R, 16R, 18R, 20R, 22R, 24R, 26R differ from one another. In some embodiments, most or all of dimensions 12F, 14F, 16F, 18F, 20F, 22F, 24F, and 26F differ from one another.

In FIG. 1, the calculated dimensions 12R, 14R, 16R, 18R, 20R, 22R, 24R, 26R and dimensions 12F, 14F, 16F, 18F, 20F, 22F, 24F, and 26F are designed to produce a circumferential garment portion when front panel 2 is joined to rear panel 4 to form seams, such that the circumferential garment portion provide desired compression effects when worn by a typical wearer. Similarly, in FIG. 2, the calculated dimensions 112R, 114R, 116R, 118R, 120R, 122R, 124R, 126R and dimensions 112F, 114F, 116F, 118F, 120F, 122F, 124F, and 126F are made based on an engineered pattern design and are designed to provide desired compression effects when front panel 102 is joined to rear panel 104 to form seams and produce a circumferential garment portion when worn by a typical wearer. Various circumferential garments or circumferential garment portions may be formed. By circumferential portion or circumferential garment portion, it is meant that the garment or portion surrounds a wearer's body part such as an arm, leg, torso, ankle, knee, elbow and so forth.

The dimensions may continually increase along one axial or longitudinal direction 28 or they may both increase and decrease along an axial direction, i.e. the dimensions neither continuously increase nor decrease along one axial or longitudinal direction 28 as shown in FIG. 3. Stated alternatively, in some embodiments, proceeding along the axial direction 28, the dimension of the engineered garment first increases between two successive locations then decreases, e.g. it increases from location 22 to 20 and then decreases from location 20 and 18. In other words, the minimum and/or maximum dimension may lie somewhere in the middle, not at either of the extreme locations 12 or 26. In some embodiments, the dimensions increase, then decrease then increase a number of times along axial direction 28.

The following description applies to both the embodiment shown in FIG. 1 and the embodiments shown in FIGS. 2 and 3 but for the sake of brevity and clarity of description, the following description will continue to be made with respect to FIG. 1.

The calculated dimensions are calculated to provide a total dimension along the circumferential dimension of a circumferential portion of a compression garment. In some embodiments in which both front panel 2 and rear panel 4 are used, the total circumferential dimension will be, for example at location 14, the total of dimensions 14 F and 14 R. According to embodiments in which two panels such as front panel 2 and rear panel 4 are used, the panels are joined to form a seam that extends along the longitudinal i.e. axial direction of the circumferential portion of the garment. In other words, the two panels are not joined to form a seam in the circumferential direction. In some embodiments in which only one panel is used and its opposed edges are joined to one another, one calculated dimension represents the total circumferential length such as dimensions 12C, 14C and 16C as will be shown in FIG. 5. For example, if only rear panel 4 is used to form a circumferential portion of a compression garment, dimension 14F itself represents the total dimension along the circumferential dimension at location 14.

Referring again to FIG. 1, the garment dimensions that determine the geometric cuts used to produce the opposed edges 6A and 6B and opposed edges 8A and 8B, may be made based upon several factors and the various factors may be factored in various mathematical formulas or algorithms.

In some embodiments, one factor is the stress-strain characteristics of fabric 10, as discussed above. The relationship between the stress and strain that a particular material displays is known as that particular material's stress-strain curve. The stress-strain curve is unique for each material and is found by recording the amount of deformation (strain) at distinct intervals of tensile or compressive loading (stress). The stress-strain curve is often presented using a curve generated according to the best fit formula. The best fit formula curve enables a better estimation of other data points in the stress-strain relationship. These curves reveal many of the properties of a material including the Modulus of Elasticity, E, and illustrate various stress-strain characteristics that may be considered as factors in determining the geometric cuts. The stress-strain curves may be used to reveal fabric compressive force F associated with a particular amount of deformation. Fabric compressive force F, is based the degree of stretching which will depend on the stretched size, i.e. size of the user's anatomy, relative to the circumferential length of the garment in a relaxed state, at a particular location. Fabric compressive force, F, can be used together with circumference "U" to predict garment compression P as will be seen in equation (1).

Referring to equation (1), each of locations 12, 14, 16, 18, 20, 22, 24, and 26, may represent a measuring point, "i", at which the garment compression, P, and the desired garment length, may be calculated. As indicated herein, the calculation may be made at various other numbers of locations instead of the exemplary eight locations listed herein, in other embodiments.

As above, the compression exerted on the wearer body part in the circumferential direction, i.e. garment compression, P, can be calculated from Equation (1), which provides:

$$Pi = \frac{20\pi^* F_i}{U_i} \quad \text{Equation (1)}$$

P = Garment Compression in kPa at measuring point $i$

F = garment compressive force in N/cm at measuring point $i$

U = circumference of garment in cm at measuring point $i$

Figure 11:
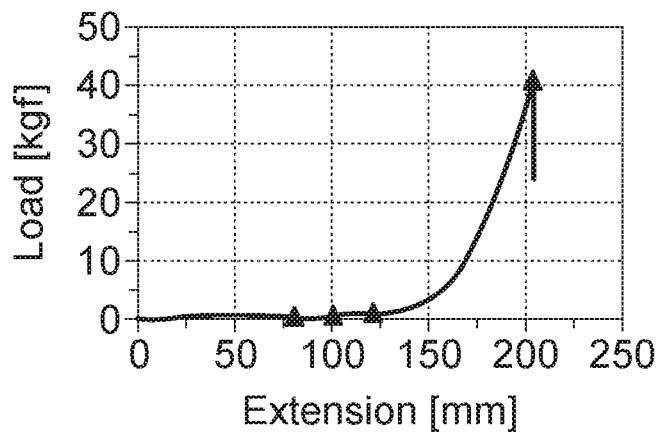
FIG. 11 shows examples of stress-strain curves.
Figure 11:
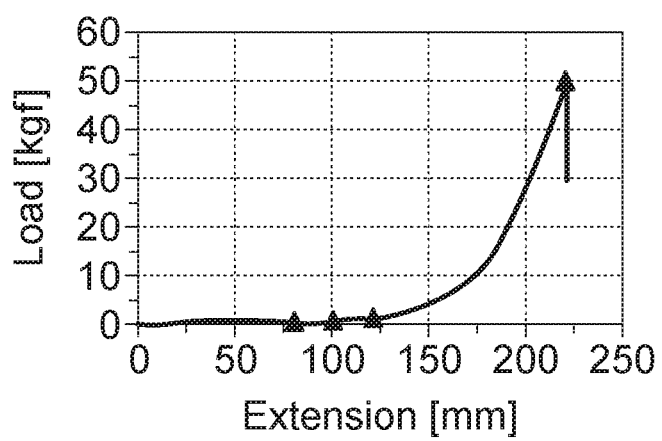

Garment compression is exerted when the garment is in a stretched state such as when worn by a wearer and in this state, U, the circumference of the stressed, i.e. stretched garment at measuring point i, is the same as the circumference of the body part at measuring point i. Garment compressive force, F, is determined by the degree of stretching of the garment. The degree of stretching can be converted to garment compressive force, F, using stress-strain curves which show garment compressive force as a function of the degree of stretching. FIG. 11 shows an example stress-strain curve. The degree of stretching depends on the length of the stretched garment in comparison to the relaxed length of the garment and this depends on the size of the wearer's anatomy, at a particular measurement location i. Once the degree of stretching is determined, it can be used in conjunction with a stress-strain curve associated with a particular fabric, to yield a garment compressive force, F, value. Equation (1) shows that different degrees of stretching (associated with different degrees of garment compressive force F) can provide the same garment compression, P, at locations where the circumference, U, varies.

The circumference of the wearer's anatomy such as a leg, which equals the stretched circumferential lengths (U) of the garment when in a stressed state as worn by the wearer, is a length that can be measured using any conventional measurement means. The degree of stretching may be expressed as [(U,stretched−U,relaxed)/U relaxed] in some embodiments and it may be expressed as (U,stretched/U, relaxed) in other embodiments depending on the mathematical formula used. The degree of stretching can be measured by comparing the stretched length to the relaxed length using any conventional measurement tool.

The value of F increases as the stretched circumferential length, U, increases in order to provide the same garment compression P according to equation (1). The degree of stretching varies with garment compressive force F according to the stress-strain curves.

P, the garment compression in kPa, can be measured at the various measuring points, i, when in a stressed state. In some embodiments, various suitable devices such as MST Professional by Swisslastic and Hosy by Hohenstein Institute, can be used to measure P, the garment compression but other suitable devices may be used in other embodiments. For example, the Hatra measurement tool measures compression according to UK standards, and Pico Press is a portable compression measuring device that may be used. The Hosy device also measures compressive force, F, and may provide these measurements along with garment compression P.

The stress-strain curve may also be used in conjunction with the known or desired garment compression P, a measured fabric compressive force, F, and a known anatomical dimension such as U in equation (1), to determine the relaxed garment dimensions, e.g. dimensions 12R, 14R, 16R, 18R, 20R, 22R, 24R, 26R, necessary to produce the desired garment compression P. According to one embodiment, the values for garment compression P and U (circumference of garment in cm at measuring point i in stretched condition) are obtained, and equation (1) is used to solve for F. With the value of F determined, the stress-strain curve can be consulted to determine the amount of stretch and since the stretch amount is known (U), the relaxed, i.e. unstretched length, can be obtained.

One factor that may be considered in determining the desired garment compression P and, therefore garment dimensions, at the various locations, is the desired compression class. Compression is a pressure, often described in units of millimeters mercury (mmHg) and may be grouped into various categories or classes, each associated with a range of compression force, e.g. 8-15 mmHg, 15-20 mmHg, 20-30 mmHg, 25-35 mmHg, 30-40 mmHg, 40-50 mmHg and higher. According to some conventions, compression class 1 is defined as a compression of 20-30 mmHg, compression class 2 is defined as 30-40 mmHg, compression class 3 is defined as 40-50 mmHg and compression class 4 is defined as higher than 50 mmHg. According to some conventions, 8-15 mmHg is referred to as mild compression and 15-20 mmHg is referred to as moderate compression. Other conventions and definitions of compression classes may be used but, regardless of how the compression classes are defined, one of the factors that may be considered in calculating the dimensions and therefore the geometric cuts, is the compression class desired for a particular body part location.

Another factor that may be utilized in determining the desired garment compression P and thus the desired dimensions, is a size chart. An industry standard size chart for a particular garment size, basically associates the size, for example "men's jeans size L" with particular dimensions of the wearer's anatomy at various locations and is generally standard, though it may vary from manufacturer to manufacturer, or region to region. For example, size "M" in Japan may be associated with different dimensions of a human body than size "M" in the United States. A size chart may indicate that in the United States, size "M" for men's jeans is associated with particular dimensions at particular locations of a man's leg.

Measurement charts represent particular dimensions for a particular garment such as a particular style of jeans, at a particular size. The measurement charts are associated with a typical wearer's size and provide associated garment dimensions at various locations of the garment, and can vary from product to product even within a single manufacturer. The measurement chart is typically both manufacturer specific and product specific and in the present invention, the measurement chart is determined according to the methods and principles of the disclosed invention and may vary for different garment types and different fabrics. A measurement chart may, for example, provide particular garment dimensions at particular locations for a woman's size "Z" for dress slacks in the United States.

For a particular garment, the calculation of a garment dimension required to yield a desired compression value "P", may involve using size information of a wearer associated with a particular size chart size, i.e. "U" in Equation (1), to calculate garment compressive force, "F" in Equation (1) and then, using the stress-strain curve and the stretched garment dimension, the necessary relaxed garment circumference required to produce the desired compression value is determined.

Additional factors taken into account to determine garment compression P include correction factors such as seam corrections and other corrections. Seam corrections take into account the impact that seam formation has upon the stretchable garment, in particular, the impact that a particular seam has upon the compression characteristics of a garment. Other correction factors may be considered as factors in determining the geometric cuts and such factors may be fabric specific, brand or manufacturer specific or product specific correction factors.

Other factors that may be considered in other embodiments include factors such as manufacturer or brand specific selected compression class, selected compression standard, selected size charts and various other factors.

The factors listed above may be used in various combinations and in various formulas and algorithms such as Equation (1) above, to estimate or calculate garment compressive force, F and garment compression P and stretched and unstretched (relaxed) garment dimensions.

The factors listed above should be considered to be illustrative but not limiting of the various factors that may be used in conjunction with various mathematical formulae, for determining/calculating the desired garment compression and, dimensions. Once the desired garment dimensions are determined, the geometric cuts can be made to produce the desired dimensions which yield the desired compressive force and garment compression values at various locations along the longitudinal direction of a worn compression garment. In some embodiments, two or more of the above-listed factors are considered and may be considered in conjunction with other factors. In some embodiments, the different factors are weighted differently in calculating how to make the geometric cuts to produce the desired garment dimensions.

In some embodiments, the factors presented in Equation (1) or other formulas, are used to determine the desired widths of front panel 2 and rear panel 4 needed to produce a desired compression at various locations, such as the above-indicated locations. Fabric 10 is cut to produce panels having the desired dimensions at the identified locations. In some embodiments, the geometric cuts include geometric cuts to both of opposed edges which may both be nonlinear edges. In other embodiments, one of the opposed edges may remain a straight or conventional cut while the other of opposed edges is non-linear, curved, partially curved or also straight, as a result of the geometric cuts made to achieve the desired circumferential lengths of the fabric, based on the engineered pattern design according to the disclosure. In some embodiments, complementary geometric cuts may be advantageously made on the corresponding edges of the respective panels 2, 4 that will be joined together, for improved ease of joining the respective panels 2, 4 together by sewing or other means.

Example

One example of a method for determining garment dimensions and making the geometric cuts to produce the desired garment dimensions using an engineered pattern design, is as follows.

Once a fabric is selected, the fabric stress-strain curve and the best fit formula for the fabric are obtained.

Next, in some embodiments, a sample compression garment is actually made with the selected fabric. The sample compression garment is circumferential, i.e. tubular in form. The circumferential length of the sample compression garment in a relaxed state is then measured at multiple measurement points such as at locations 12, 14, 16, 18, 20, 22, 24, and 26. These circumferential measurements from the sample compression garment in a relaxed state, may be compared to a size or measurement chart for a particular size of the garment at each of locations 12, 14, 16, 18, 20, 22, 24, and 26 to determine degree of stretch, in various embodiments, because the size chart represents the circumferential length of a typical wearer for a particular size, at each of the indicated locations and this is equal to the stretched length of the garment when stretched as worn by a wearer. According to some embodiments, the sample compression garment is then tested, i.e. the actual garment compression P is measured at each of locations 12, 14, 16, 18, 20, 22, 24, and 26 when the garment is in a stretched state such as on a body model member having the same dimensions in accordance with a size chart. The garment compression measurements may be expressed as a pressure such as kPa, kilopascals (Newtons/(centimeter-squared)), or mmHg, in various embodiments.

In one embodiment, the actual garment compression P at each of locations 12, 14, 16, 18, 20, 22, 24, and 26 is measured in units of pressure such as mmHg, and converted from pressure to garment compressive force, F using the following formula: F=[(measured pressure)×(size measurements from size chart)/470] which produces garment compressive force F in units of N/cm. In other embodiments, the actual garment compression P is measured in units of kPa and is converted from pressure to garment compressive force F using size measurements from size or measurement chart in Equation (1), above. According to either embodiment, garment compressive force F is now determined. The invention is not limited to the above calculations and other units and other conversions may be used to measure garment compression P and calculate garment compressive force F, in other embodiments.

The degree of elongation is determined by comparing the stretched garment circumferential length based on the size chart, and the relaxed sample compression garment length at each of the locations 12, 14, 16, 18, 20, 22, 24, and 26, the elongation being the ratio of the stretched circumferential length, i.e. the size of the wearer's anatomy "U" for a tight-fitting garment, to the relaxed garment measurements. In some embodiments, the elongation is represented by [(U,stretched−U,relaxed)/U,relaxed] at each of the locations 12, 14, 16, 18, 20, 22, 24, and 26. The stretched sample compression garment circumferential lengths may be determined by either consulting the size chart or by measuring the length of the stretched sample compression garment on a body model member having the dimensions of a size chart associated with a particular size. The two lengths (stretched garment circumferential length and relaxed garment circumferential length) reveal the degree of stretching and can be used with stress-strain curves to predict the fabric compressive force, f, at locations 12, 14, 16, 18, 20, 22, 24, and 26.

A seam correction factor may be obtained by comparing a) the garment compressive force F obtained using the measured garment compression P, to b) the fabric compressive force f garnered from the stress-strain curve at locations 12, 14, 16, 18, 20, 22, 24, 26, as above based on the degree of stretching.

Desired garment compression P, in pressure, is then identified for each location 12, 14, 16, 18, 20, 22, 24, and 26.

The garment compressive force, F required to produce the desired garment compression P, is then calculated using the desired garment compression, expressed as a pressure, and standard size chart measurements at each location using Equation (1), for example, when the desired garment compression is identified in pressure units kPa. The garment compressive force, F, is then converted to fabric compressive force, f, by multiplying the garment compressive force F by the seam correction factor at each location 12, 14, 16, 18, 20, 22, 24, and 26.

The stress-strain curve is then used to associate this fabric compressive force, f, with a degree of elongation at each location 12, 14, 16, 18, 20, 22, 24, and 26. With the degree of elongation known and the stretched garment length known as according to size charts, the relaxed length of the garment that will provide the desired garment compression P can be determined at each location.

The compression garment or the circumferential portion of the compression garment is then formed by making geometric cuts to the fabric to produce one or more fabric panels that include relaxed garment length measurements as determined above. The method for determining the relaxed garment lengths is described in FIGS. 10A and 10B, below.

Note that the preceding is just one embodiment, using a fabricated sample compression garment, for determining the required garment measurements at suitable locations along the garment based on desired compression values at various locations of the garment and various other factors. In other embodiments, various other methods and techniques are used to determine the desired garment dimensions based on desired compression values at various locations. In many embodiments, a fabricated sample garment is not necessary and the garment dimensions are based on various of the preceding factors.

DETAILED DESCRIPTION

In some embodiments, the desired garment compression value at each of locations 12, 14, 16, 18, 20, 22, 24, and 26 is defined for the garment according to the desired compression class or other compression levels and compression standards. The compression values at each of locations 12, 14, 16, 18, 20, 22, 24, and 26 are chosen to combine to provide a compression garment that provides the maximum therapeutic advantage.

In advantageous embodiments, the produced compression values are the same at each of locations 12, 14, 16, 18, 20, 22, 24, and 26, i.e. uniform compression is provided to a wearer. In this advantageous embodiment, the degree of stretching can vary at various locations as predicted by equation (1). In some embodiments, the different degrees of stretching include degrees of stretching that increase then decrease then increase along one or more groups of three successive axial locations, when the compression garment is in the stretched state as worn by the wearer.

In this case in which garment compression P remains constant and U varies and garment compressive force F will also vary as will the degree of stretching.

In other embodiments, the produced compression values are different at one or more or all of locations 12, 14, 16, 18, 20, 22, 24, and 26. According to such embodiments, the different compression values at the different locations may vary gradually, abruptly or irregularly in various embodiments. The compression values may continually increase along one axial or longitudinal direction 28 to produce a gradient of compression. Alternatively, the compression values may both increase and decrease along an axial direction. In some embodiments, the compression values neither continuously increase nor continuously decrease along one axial or longitudinal direction 28. In other words, the maximum or minimum garment compression value is not at one end of the garment, but may be at some intermediate location in some non-uniform compression embodiments. Geometric cuts are made to fabric 10 to produce front panel 2 and rear panel 4 based on the garment dimensions required to produce the desired garment compression values.

The garment dimensions determined to produce the desired garment compression, represent the circumferential length determined for various axial locations of the circumferential portion of the compression garment. In some embodiments in which only one panel, e.g. front panel 2 or rear panel 4, is used, the circumferential length represents one of the garment dimensions (12F, 14F, 16F, 18F, 20F, 22F, 24F, 26F, 12R, 14R, 16R, 18R, 20R, 22R, 24R, 26R) indicated above. In other embodiments in which front panel 2 is joined to rear panel 4, the circumferential length is a total circumferential length when the two panels are joined together. For example, the total circumferential length at location 16 is the sum of garment dimension 16F and garment dimension 16R because the two panels are joined together at the indicated locations. The circumferential lengths will be shown as circumferential lengths 12C, 14C, 16C, 18C, 20C, 22C and 24C in FIG. 5.

The geometric cuts are made based on the determined garment dimensions to produce the garment dimensions 12F, 14F, 16F, 18F, 20F, 22F, 24F, 26F, 12R, 14R, 16R, 18R, 20R, 22R, 24R, 26R at various locations of the garment.

According to one embodiment, after fabric 10 is geometrically cut to produce front panel 2 and rear panel 4, the panels are formed into a circumferential member, a pant leg in the case of the illustrated embodiment, by forming seams by joining the respective edges of front panel 2 and rear panel 4.

Figure 4:
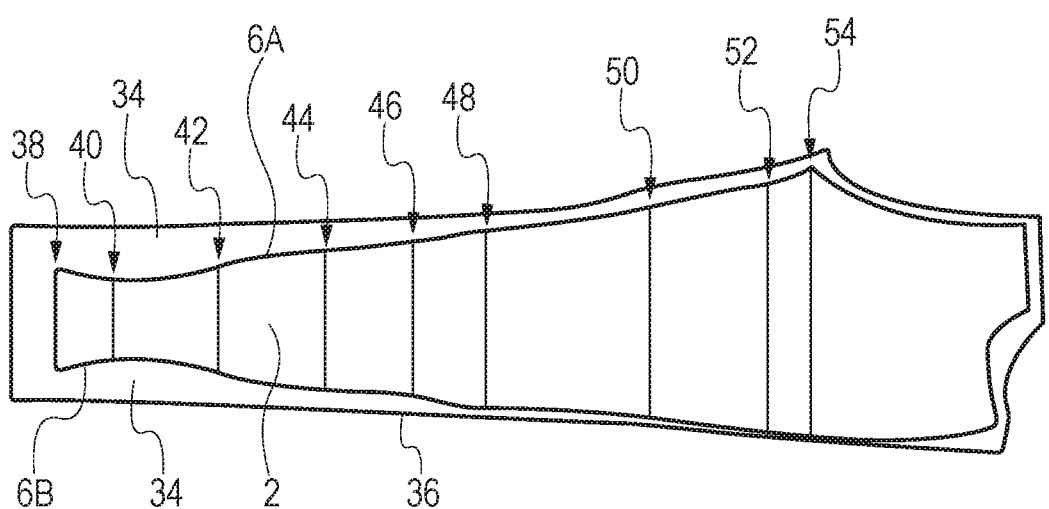
FIG. 4 shows a comparison between a conventionally cut pant leg and an embodiment of a panel of fabric that is a portion of a pant leg having dimensions determined and cut, in accordance to embodiments of the disclosure.

FIG. 4 presents a comparison between front panel 2 formed according to embodiments of the disclosure, and a conventionally cut front panel 34. FIG. 4 shows that the outer edges 36 of conventionally cut front panel 34 are significantly different than opposed edges 6A, 6B of front panel 2. The difference between the cuts of the front panel 2 formed according to the disclosure and the conventional front cut panel 34 can be noted at various locations including at arbitrary locations 38, 40, 42, 44, 46, 48, 50, 52 and 54 which may be locations at which particular dimensions of front panel 2 were determined according to the disclosure. Other locations are used in other embodiments.

Figure 5:
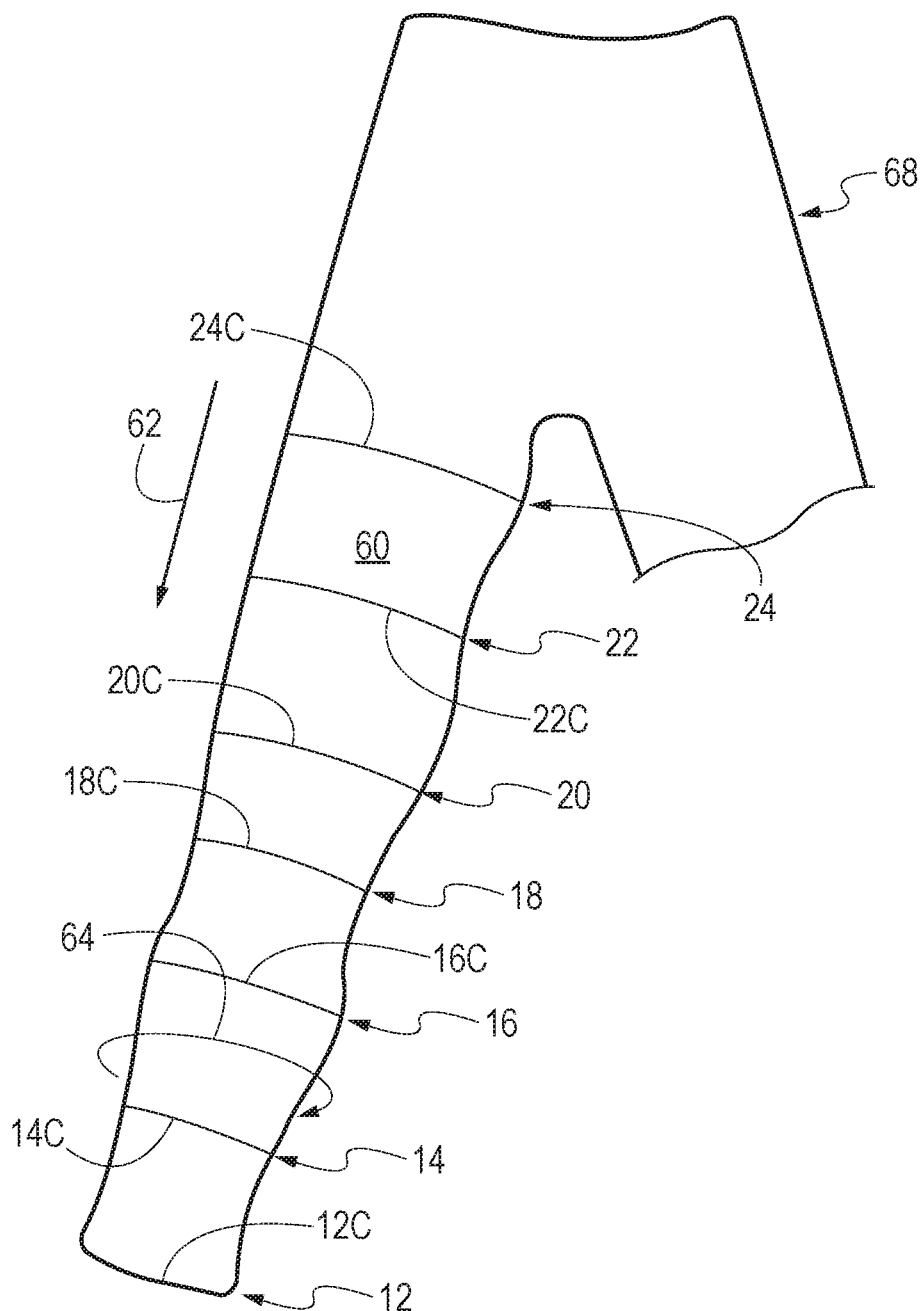
FIG. 5 shows two pieces of stretchable fabric joined together to form a pant leg according to an embodiment of the disclosure.

FIG. 5 shows of two panels of fabric 10 such as shown in FIG. 1, formed into a circumferential member, i.e. pant leg 60 of a compression garment which is a pair of pants 68, in the illustrated embodiment. In other embodiments, other compression garments are formed. According to other embodiments, other circumferential portions of compression garments or other compression garments, may be formed. Pant leg 60 is defined by axial direction 62 and circumferential direction 64 and is a circumferential garment portion that may alternatively be referred to as a tubular or cylindrical garment portion. Circumferential member, i.e. pant leg 60 in its relaxed state such as shown in FIG. 5 does not have a straight outer edge in axial direction 62. Rather, locations 12, 14, 16, 18, 20, 22 and 24, such as shown in FIG. 1, have different widths, i.e. different lengths along circumferential direction 64. At locations 12, 14, 16, 18, 20, 22, and 24, pant leg 60 has different circumferential lengths 12C, 14C, 16C, 18C, 20C, 22C and 24C. This is due to the geometric cut of edges 6A, 6B, 8A and 8B as shown in FIG. 1 and discussed above.

Again referring to FIG. 5, pant leg 60 is narrower at location 18 than at location 16, i.e. pant leg 60 has a lesser length at location 18 in the circumferential direction 64, than at location 16, when pant leg 60 is in a relaxed state. In advantageous embodiments, the fabric of pant leg 60 includes constant elastic properties (i.e., uniform elasticity) and is characterized as having a plurality of zones or circumferential bands at locations 12, 14, 16, 18, 20, 22, and 24 that are substantially parallel to one another and transverse to axial direction 62, the circumferential bands including different lengths of fabric 10. FIG. 5 also shows that the circumferential length of fabric both increases and decreases along one direction of the axial direction 62 as illustrated, and also along the opposite axial direction. The same may be true for the degree of stretching of pant leg 60 when worn. In other words, the circumferential lengths 12C, 14C, 16C, 18C, 20C, 22C and 24C neither continuously increase nor continuously decrease along one axial or longitudinal direction 28 when in a relaxed state. Stated alternatively, in some embodiments, proceeding along the axial direction 28, the circumferential length of the engineered garment first increases between two successive locations then decreases, e.g. it increases from location 22 to 20 and then decreases from location 20 to 18 when in a relaxed state. In other words, the maximum and/or minimum dimensions may be at an intermediate location such as location 16, 20 or 22, for example.

In other embodiments, the circumferential length of pant leg 60 constantly increases or decreases along the axial direction 62 to produce a gradient along an axial direction.

According to either of the aforementioned embodiments, the compression may be the same at the various locations 12, 14, 16, 18, 20, 22, 24, and 26 even though the degree of stretching will vary when worn by a wearer. The circumferential dimensions of pant leg 60 may be the same or may differ at locations 12, 14, 16, 18, 20, 22, 24, and 26, and may produce a circumferential garment compression that is the same at all locations or which varies at the various locations.

Figure 5A:
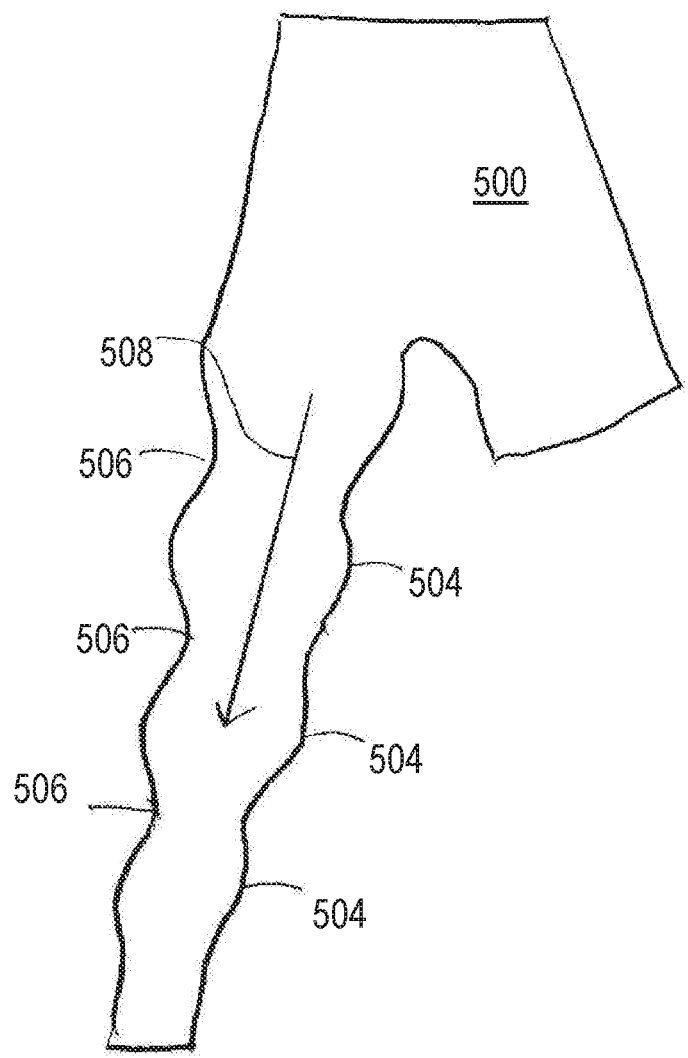
FIG. 5A shows an embodiment of a compression garment having ridged features in a relaxed state but which provides uniform compression to a wearer.

FIG. 5A shows an embodiment of a compression possible according to the methods of the invention. The compression garment has ridged features in a relaxed state but which provides uniform compression to a wearer. Compression garment 500 is a pair of pants formed according to the methods of the invention, in a relaxed state. Compression garment 500 provides uniform compression along the leg portion 502. In a relaxed state, leg portion 502 includes undulations marked by rigid portions 504 and valley portions 506. When stressed as worn by a wearer, different locations along the axial direction 508 of compression garment 500, stretch to different degrees but provide the same garment compression P.

Figure 6:
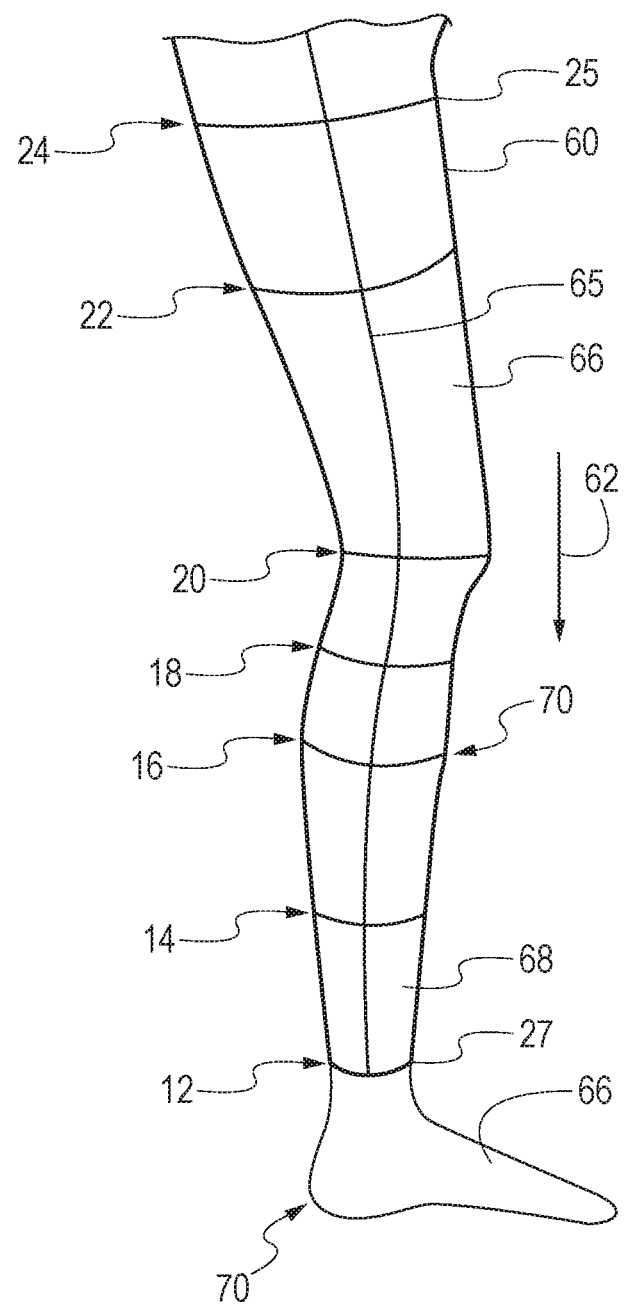
FIG. 6 shows an embodiment of a pant leg of a compressive garment formed according to the disclosure, as worn by a typical wearer.

FIG. 6 shows a circumferential member, pant leg 60 in a stressed state as tightly worn on a body part of wearer 70, a typical wearer of the garment. The body part is a leg of a human but according to other exemplary embodiments, the circumferential member may be worn on other parts of the human anatomy or on other animals. FIG. 6 shows that pant leg 60 of pants 68 includes some straight outer surfaces in the axial direction 62 at some locations that correspond to straight locations of the wearer's body, i.e. leg 66, when worn by a wearer, as the pant leg 60 is worn tightly by wearer 70 and conforms to the shape of the wearer's body part. Pant leg 60 is a circumferential, i.e. tubular or cylindrical garment portion and may be formed of one or two fabric panels joined to form a seam 65, each of the fabric panels extending completely from one longitudinal end, to another, i.e. from location 25 to location 27. Seam 65 extends in the axial direct action 62 and may be a chain stitch, safety stitch or overlapped stitch in some embodiments, but any of the various seam types described above may be used. Seam 65 is illustrated in an exemplary location only and may be placed at other locations in other embodiments.

In some embodiments, pant leg 60 may stretch to different degrees at the respective locations 12, 14, 16, 18, 20, 22, 24, and 26 and be characterized as applying the same compression at each of the respective locations 12, 14, 16, 18, 20, 22, 24, and 26, based on the degree of stretching and relaxed garment dimensions. According to each of the described embodiments, the elasticity of the fabric may be uniform throughout the fabric.

As such, various embodiments can be understood with respect to FIG. 6. In some embodiments in which the applied compression is nonuniform, the degree of compression in the circumferential direction varies and may have a maximum and/or a minimum at an end location such as at location 12 or 24, when in a stressed state such as when worn by a wearer. The garment compression may both increase and decrease along an axial direction 62 and the compression profile may be characterized in that the compression values may increase, then decrease, then increase along at least one group of 3 successive axial locations such as axial locations 16, 18, and 20. The applied circumferential garment compression may continuously increase or decrease to form a compression gradient along an axial direction of the wearer's body part.

In advantageous embodiments, the geometric cuts produce a circumferential compression garment with the same circumferential compression, i.e. the same garment compression P, throughout the length of the compression garment.

In other embodiments, the circumferential member forms a compression garment or a part of a compression garment other than a pant leg such as shown in the figures. In some embodiments, the circumferential member is formed of two or more fabric panels that each extend along the entire longitudinal length of the circumferential member while in some embodiments, the circumferential member of the compression garment comprises a single piece of woven fabric 10.

Figure 7:
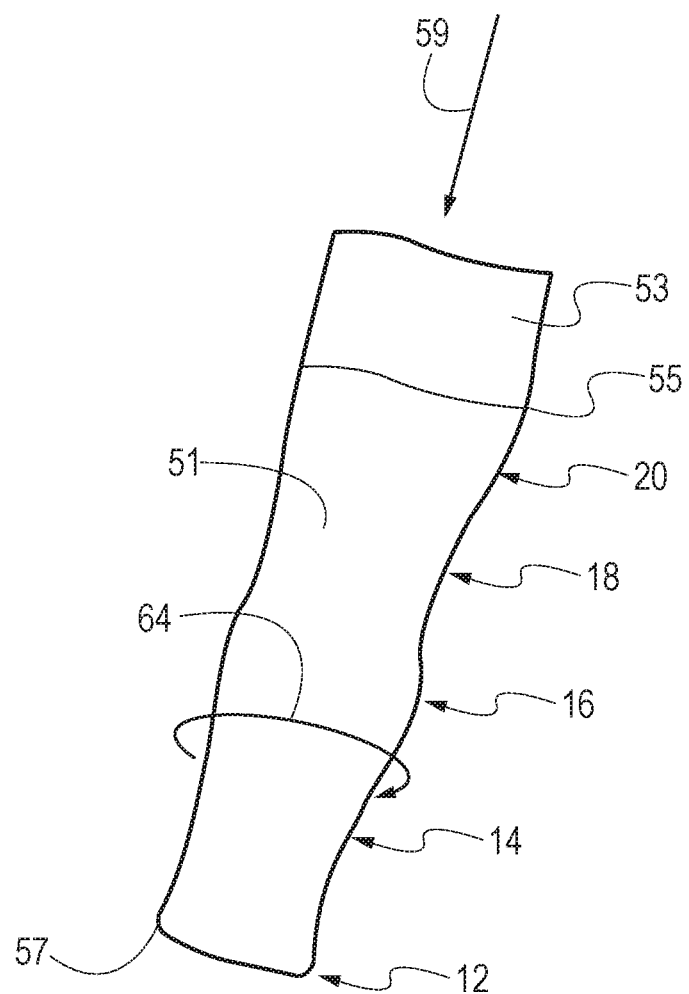
FIG. 7 shows a garment portion formed of a cylindrical compressive garment portion formed of a stretchable elastic material joined to a cylindrical garment portion formed of inelastic material.

FIG. 7 shows another embodiment of a compression garment according to the disclosure. FIG. 7 shows circumferential garment portion 51 of pant leg 60 described above and having the same circumferential compression (garment compression P) applied by the garment at the various axial locations 12, 14, 16, 18 and 20. Circumferential garment portion 51 may be formed of one or multiple pieces of fabric each of which extend from one longitudinal end 55 to the other longitudinal end 57. Joined to circumferential garment portion 51 is a further circumferential garment portion 53. Further circumferential garment portion 53 may be a non-compression garment portion i.e. further circumferential garment portion 53 may be formed of a non-elastic fabric. Further circumferential garment portion 53 is longitudinally joined to circumferential garment portion 51 at longitudinal end 55 and shares a common axis 59 with circumferential garment portion 51. According to this embodiment, the garment formed is a combination of circumferential garment portion 51 with uniform compression and further circumferential garment portion 53.

Figure 8:
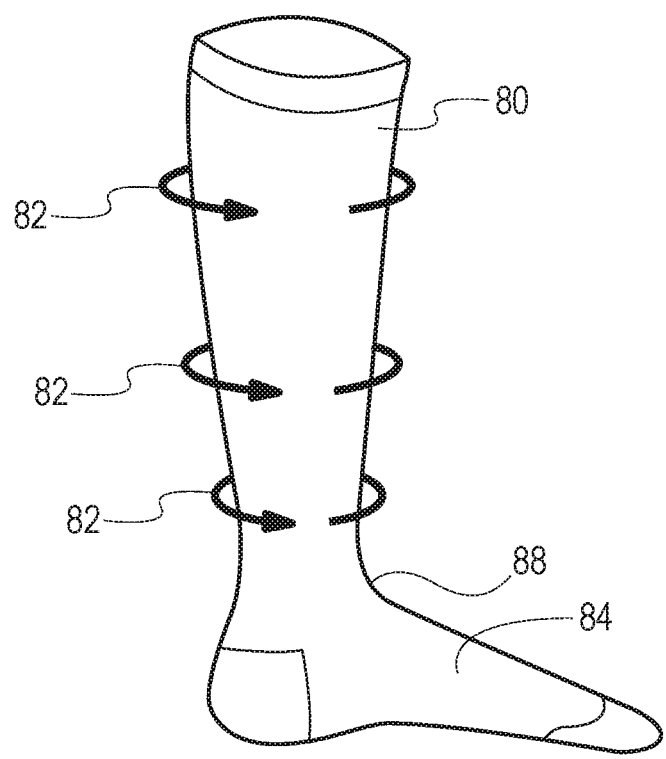
FIG. 8 shows a compression sock embodiment of a compressive garment formed according to the disclosure.

FIG. 8 shows a compression sock 80 embodiment of a compressive garment formed according to the disclosure. Compression sock 80 may be formed according to any of the described methods and may have various degrees of compression or uniform compression when in a stressed condition such as worn by a wearer. In some embodiments, compression sock 80 may not include foot portion 84 and may be more of a sleeve that covers the wearer's lower leg and extends downward only to ankle location 88.

Figure 9:
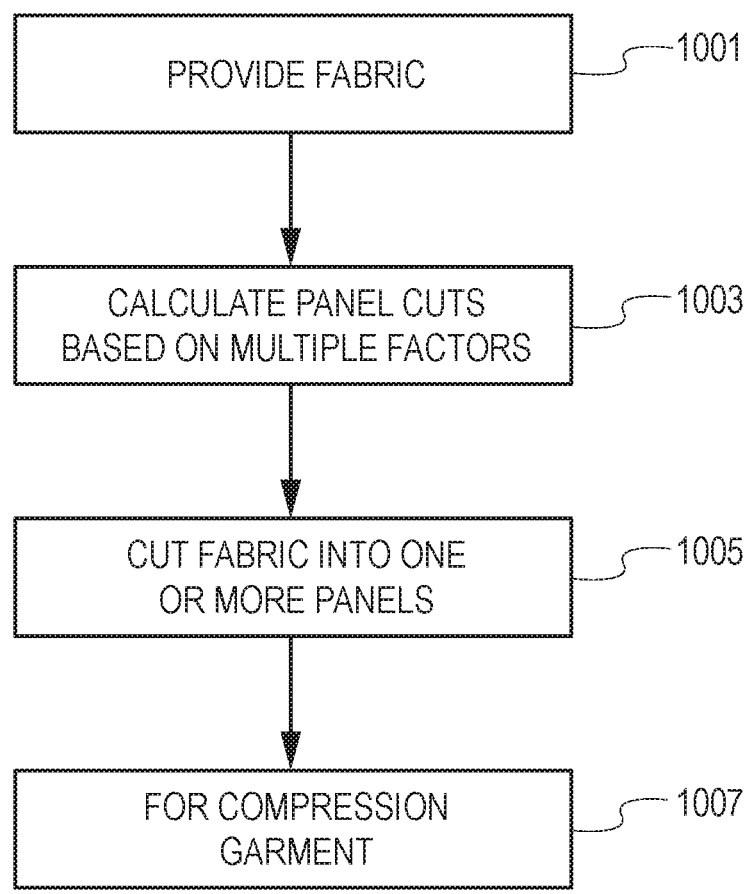
FIG. 9 is a flow chart showing aspects of a method used to form a compression garment in accordance with the disclosure.

FIG. 9 is a flowchart that illustrates a method for forming a compression garment according to the disclosure. At step 1001, fabric is provided. The fabric is a stretchable fabric and may be fabric 10 described above. At step 1003, fabric cuts, i.e. geometric cuts, are calculated. More particularly, the dimensions of the garment at various locations are determined based on a number of factors such as described above. One or multiple geometric cuts are made to produce one or more fabric panels to produce the desired dimensions. Various mathematical formulas and/or algorithms are used to generate the panel cuts from the factors. The cuts are designed to provide desired compression values at the various different locations of the garment. At step 1005, the fabric is cut into one or more panels. One or more of the panels may include variously shaped edges as described above. At step 1007, a compression garment is formed using the one or more panels. The compression garment includes a circumferential portion that surrounds a body part of a wearer. In some embodiments, the circumferential portion is formed by joining edges of a single fabric panel to form a circumferential portion with a single seam and in other embodiments, the circumferential portion is formed by joining a plurality of pieces of fabric including the panel with at least one non-linear edge. The degree of stretching of the fabric at the various locations may be the same or may differ when worn, as a result of the various lengths of material in the circumferential direction, e.g. lengths 12F, 14F, 16F, 18F, 20F, 22F, 24F, 26F, 12R, 14R, 16R, 18R, 20R, 22R, 24R, 26R as in FIG. 1. In one advantageous embodiment, the degrees of stretching vary at the different axial locations but the garment compression P is the same.

Figure 10A:
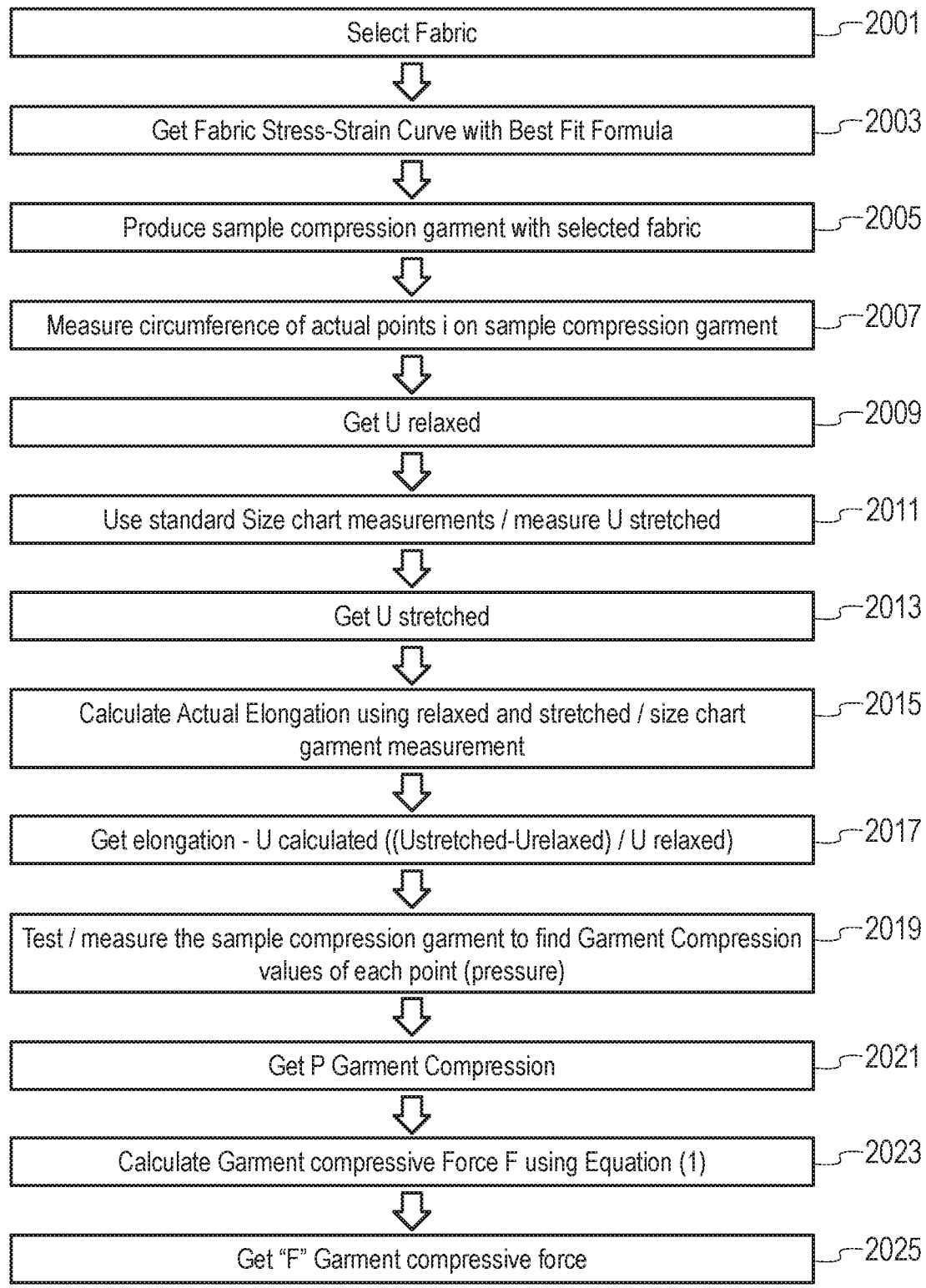
FIGS. 10A and 10B together present a flow chart showing additional details of a method used to form a compression garment in accordance with the disclosure.
Figure 10B:
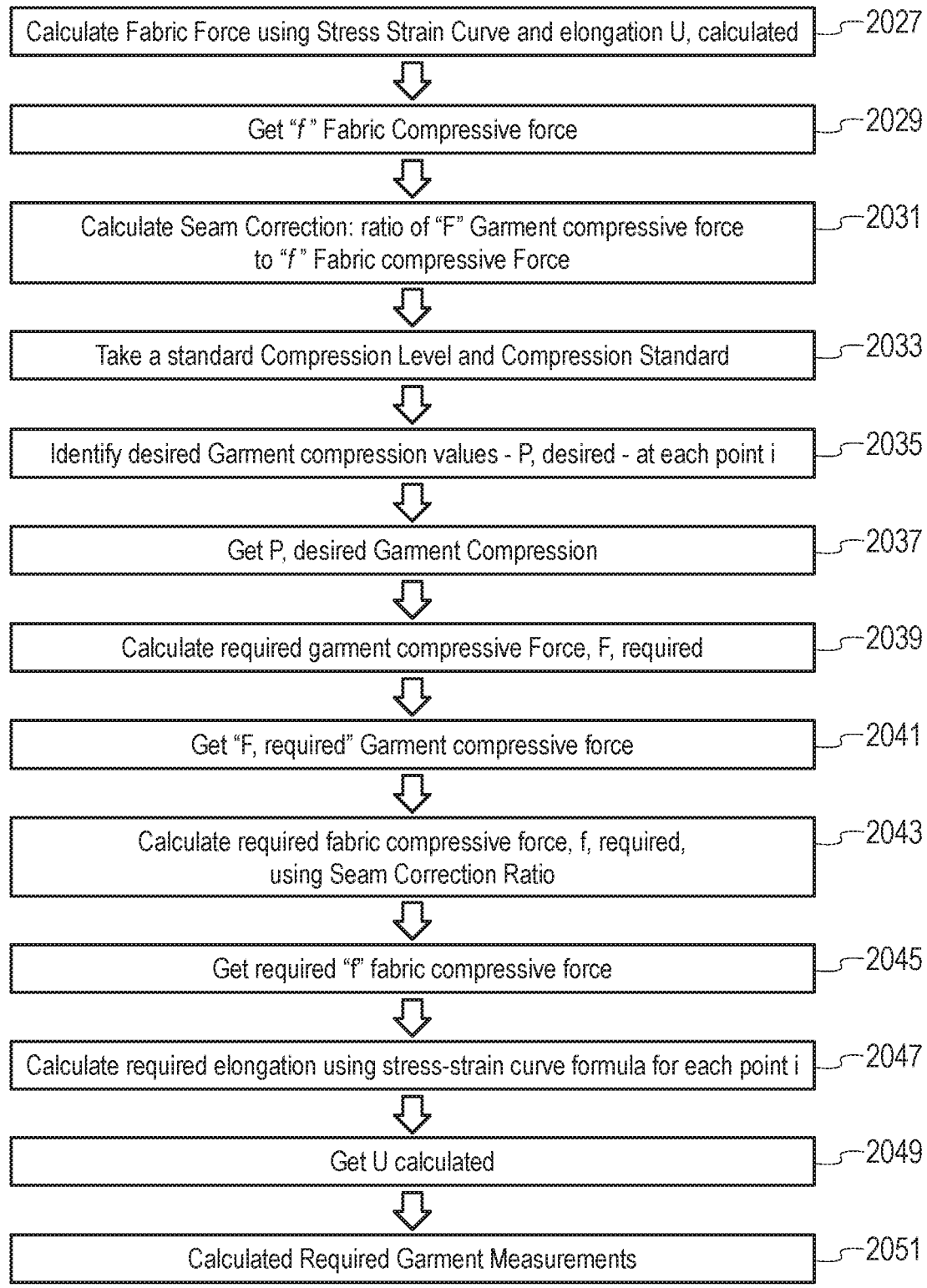

FIGS. 10A and 10B together present a flowchart for performing a sequence of operations and various calculations for making the geometric cuts to produce the compression garment, according to Equation (1).

At step 2001, select fabric, a stretchable woven fabric having a uniform elasticity such as described above, is chosen. At step 2003, a fabric stress-strain curve generated using the best fit formula, is obtained for the selected fabric. At step 2005, a sample compression garment is formed with the selected fabric. The sample compression garment is tubular, i.e. circumferential, in shape. At step 2007, the circumference of the sample compression garment is measured at multiple points, i, when the sample compression garment is in a relaxed state. The multiple points, i, represent multiple locations along the axial direction of the sample compression garment. Step 2009 indicates that U,relaxed is obtained from step 2007.

At step 2011, standard size chart measurements are obtained and may be used to identify U,stretched at each of the locations i, in which the circumference was obtained on the sample compression garment in a relaxed state. The standard size chart measurements are indicative of a wearer's anatomy and therefore represent the circumference length of the compression garment in a stretched state at various locations, when worn. In some embodiments, the sample compression garment is placed on a body part model that includes standard size chart dimensions and the sample compression garment lengths, U,stretched, are obtained at each location i. Step 2013 indicates that U,stretched was obtained at step 2011. At step 2015 actual elongation of the sample compression garment is calculated using U,stretched and U,relaxed. Step 2017 shows that actual elongation is U,calculated=((U,stretched−U,relaxed)/U relaxed) in this embodiment.

At step 2019, the garment compression exerted by the sample compression garment is measured at each point i of the sample compression garment. This pressure measurement may be in pressure units kPa, kilopascals, but other units of pressure such as mmHg, may be used in other embodiments. Garment compression, i. e., pressure, may be measured as indicated above. Step 2021 indicates that garment compression P was obtained at each point i, in step 2019.

At step 2023, garment compressive force F is calculated based on the measured garment compression P obtained in step 2019 and the actual measured circumference, U,stretched (equal to the size chart measurements) using Equation (1) with garment compression P measured in kPa. In other embodiments in which garment compression P is measured in mmHg, an equation used to calculate garment compressive force F based on garment compression P may be: garment compressive force F=(Garment Compression*U, stretched)/470. In other embodiments, other mathematical relations may be used. The calculated garment compressive force calculated in step 2023 is indicated as obtained in step 2025.

At step 2027, elongation, i.e. U,calculated is used in conjunction with the stress-strain curve to calculate fabric compressive force f at each location i, as indicated at step 2029.

At step 2031, seam correction is calculated. The seam correction is the ratio of garment compressive force F obtained in step 2025 to the fabric compressive force f as indicated in step 2029, at each location i. The seam correction factor is a pure number. At step 2033, various compression levels and compressive standards are considered and based on such considerations, at step 2035, desired garment compression is identified for each location i. At step 2037, the desired garment compression P,desired is then known for each location i.

At step 2039, the calculation described above in conjunction with steps 2023 and 2025 is carried out to determine the garment compressive force F required to produce the desired garment compression, P,desired from step 2037. Step 2041 shows that "F,required" is thereby obtained. At step 2043, at each location i, the garment compressive force F is adjusted to produce the required fabric force f. In particular, the garment compressive force F is multiplied by the seam correction factor to produce an associated fabric compressive force f such that will produce the desired garment compression P,desired. At step 2045 fabric compressive force f has been determined. With the fabric compressive force f, known, the elongation U,calculated is determined at step 2047 using the stress strain curve for the fabric. With the elongation, U,calculated known at step 2049 and the value of U,stretched known, i.e. the U values of the standard size chart measurements, the value for U,relaxed can be determined at each location I at step 2051.

These values, U,relaxed are the circumferential length values of the compressive garment or compressive garment portion being produced as above.

FIG. 11 shows two example stress-strain curves. In each stress-strain curve, garment compressive force, "load," is expressed in kgf (kilogram force) with respect to associated extension of the garment indicated on the abscissa. In the presented stress-strain curves, garment stress is expressed in millimeters of extension for a sample garment specimen of known length and the degree of stretching such as (U, stretched−U, relaxed)/U, relaxed] or (U, stretched/U, relaxed) may be calculated therefrom. In other embodiments, the degree of stretch expressed on the abscissa may represent one of the above cited formulations or as a percentage stretch. The example stress-strain curves are examples for sample specimens and various other types of stress-strain curves may be used in various embodiments.

The disclosed compression garment can be used to provide compression to a body part of a wearer. The disclosure provides a compression garment of a woven fabric with elasticity throughout and including a circumferential portion with the circumferential lengths of fabric at different axial locations tailored to produce desired compression levels at the various locations. When the garment is in a relaxed state, as described above, and as shown in FIG. 5, circumferential lengths may vary or be the same at the various locations. When in a stressed state, e.g. when worn by a wearer, the garment may stretch to different degrees or to the same degree at the various locations to provide a compression that may be the same or may vary along the axial locations, also as described above. In one advantageous embodiment, the garment stretches to different degrees at the various locations and provides a uniform compression at all axial locations. In some embodiments, the compression garment is a pair of jeans such as shown in FIGS. 5, 5A and 6. In some embodiments, the jeans are formed of stretchable denim that advantageously provides a fashionable appearance. In some embodiments, the compression garment is a pair of compression socks such as shown in FIG. 8.

The preceding merely illustrates the principles of the disclosure. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Although the invention has been described in terms of exemplary embodiments, it is not limited thereto. Rather, the appended claims should be construed broadly, to include other variants and embodiments of the disclosure, which may be made by those skilled in the art without departing from the scope and range of equivalents of the invention.

The invention claimed is:

1. A compression garment (68, 80) comprising a circumferential portion (66) formed of an uncoated, singly ply woven stretchable fabric (10) with uniform elastic properties, said circumferential portion (66) comprising at least one panel (2,4) coupled laterally to form seams that extend in an axial direction, each of the panel extends to opposite longitudinal ends of said circumferential portion and said circumferential portions are characterized as exhibiting different degrees of stretching at different axial locations of said circumferential portion but providing the same degree of garment compression (P) at each of said circumferential portions, when said compression garment is in a stressed state as worn by a wearer (70), wherein, along an axial direction of said circumferential portion (66), values for circumferential lengths (12C, 14C, 16C, 18C, 20C, 22C, 24C, 26C) of said circumferential portion first increase, then decrease, then increase, at least a plurality of times when said compression garment is in a relaxed state, wherein said degree of stretching comprises ((U,stretched−U,relaxed)/U, relaxed), U, stretched comprises stretched circumferential length of said compression garment in a stressed state when worn, and U,relaxed comprises circumferential length of said compression garment in a relaxed state.

2. The compression garment (68, 80) as in claim 1, wherein said circumferential portion includes undulations (504, 506) in the axial direction when in a relaxed state.

3. The compression garment (68, 80) as in claim 1, wherein said circumferential portion includes circumferentially extending ridges (504) along said axial locations when in a relaxed state.

4. The compression garment (68, 80) as in claim 1, wherein said circumferential portion (66) comprises no more than a single panel (2, 4) of said woven stretchable fabric.

5. The compression garment (68, 80) as in claim 1, wherein said circumferential portion (66) comprises two panels (2,4) of said woven stretchable fabric (10), joined to form seams that extend along the axial direction (28) of said circumferential portion (66), each said panel extending completely from one longitudinal end to an opposed longitudinal end of said circumferential portion.

6. The compression garment (68, 80) as in claim 1, wherein said woven stretchable fabric (10) comprises denim.

7. The compression garment as in claim 1, wherein said compression garment comprises a pair of jeans (68) and said circumferential portion comprises a thigh portion of a pant leg (60).

8. The compression garment as in claim 1, wherein said degree of garment circumferential compression (P) when said circumferential garment portion is in said stretched condition when worn by a wearer at a plurality of different axial locations (12, 14, 16, 18, 20, 22, 24, 26) is according to equation (1), $$Pi = \frac{20\pi^* F_i}{U_i} \quad (1)$$

wherein P=garment circumferential compression in kPa, F=garment compressive force in N/cm and U=value for circumferential length at each of said different axial locations (12, 14, 16, 18, 20, 22, 24, 26).

* * * * *